(12) United States Patent
Carreon et al.

(10) Patent No.: US 11,304,610 B2
(45) Date of Patent: Apr. 19, 2022

(54) BODY STATE CLASSIFICATION

(71) Applicant: Impedimed Limited, Pinkenba (AU)

(72) Inventors: Richard Roland Carreon, Fallbrook, CA (US); Jack Gerald Cosentino, Savage, MN (US)

(73) Assignee: Impedimed Limited, Pinkenba (AU)

( * ) Notice: Subject to any disclaimer, the term of this patent is extended or adjusted under 35 U.S.C. 154(b) by 395 days.

(21) Appl. No.: 15/999,047

(22) PCT Filed: Feb. 15, 2017

(86) PCT No.: PCT/AU2017/050127
§ 371 (c)(1),
(2) Date: Aug. 16, 2018

(87) PCT Pub. No.: WO2017/139838
PCT Pub. Date: Aug. 24, 2017

(65) Prior Publication Data
US 2019/0357776 A1 Nov. 28, 2019

Related U.S. Application Data

(60) Provisional application No. 62/380,236, filed on Aug. 26, 2016, provisional application No. 62/295,971, filed on Feb. 16, 2016.

(51) Int. Cl.
*A61B 5/02* (2006.01)
*A61B 5/0205* (2006.01)
(Continued)

(52) U.S. Cl.
CPC ........ *A61B 5/02055* (2013.01); *A61B 5/0022* (2013.01); *A61B 5/01* (2013.01);
(Continued)

(58) Field of Classification Search
CPC ..... A61B 5/02055; A61B 5/0022; A61B 5/01; A61B 5/0537; A61B 5/117; A61B 5/021;
(Continued)

(56) References Cited

U.S. PATENT DOCUMENTS 5,788,643 A 8/1998 Feldman
2005/0069853 A1 3/2005 Tyson et al.
(Continued)

FOREIGN PATENT DOCUMENTS

WO WO 2007/002993 1/2007

OTHER PUBLICATIONS

International Search Report and Written Opinion dated Mar. 27, 2017 for Application No. PCT/AU2017/050127.
(Continued)

*Primary Examiner* — Amanda K Hulbert
*Assistant Examiner* — Natasha Patel
(74) *Attorney, Agent, or Firm* — Knobbe, Martens, Olson & Bear, LLP

(57) ABSTRACT

A system for determining reference signatures for use in assisting identification of a body state in a biological subject, the system including at least one processing device that obtains reference data for each of a plurality of reference individuals, the reference data including at least one reference impedance indicator obtained by performing at least one impedance measurement on the reference individual, a body state indication indicative of any body states associated with the reference individual and characteristic data indicative of one or more physical characteristics of the reference individual and analyses the reference data to establish one or more reference signatures, each reference signature being indicative of at least one reference impedance indicator associated with a respective body state for respective physical characteristics.

18 Claims, 21 Drawing Sheets

(51) Int. Cl.
*G16H 50/30* (2018.01)
*G16H 80/00* (2018.01)
*A61B 5/00* (2006.01)
*A61B 5/01* (2006.01)
*A61B 5/0537* (2021.01)
*A61B 5/117* (2016.01)
*A61B 5/021* (2006.01)
*A61B 5/024* (2006.01)
*A61B 5/08* (2006.01)
*A61B 5/145* (2006.01)

(52) U.S. Cl.
CPC ............ *A61B 5/0537* (2013.01); *A61B 5/117* (2013.01); *G16H 50/30* (2018.01); *G16H 80/00* (2018.01); *A61B 5/021* (2013.01); *A61B 5/024* (2013.01); *A61B 5/0816* (2013.01); *A61B 5/14542* (2013.01); *A61B 5/14546* (2013.01)

(58) Field of Classification Search
CPC ... A61B 5/024; A61B 5/0816; A61B 5/14542; A61B 5/14546; A61B 5/4878; A61B 5/4875; A61B 5/7275; G16H 50/30; G16H 80/00; G16H 10/60; G16H 50/70; G16H 20/30; G16H 20/60
See application file for complete search history.

(56) References Cited

U.S. PATENT DOCUMENTS

| | | |
|---|---|---|
| 2007/0270707 A1 | 11/2007 | Belalcazar |
| 2008/0001735 A1* | 1/2008 | Tran ........................ G06F 19/00 340/539.22 |
| 2008/0154645 A1 | 6/2008 | Takehara |
| 2008/0188765 A1* | 8/2008 | Stolarski .................. A61B 5/35 600/518 |
| 2010/0227302 A1 | 9/2010 | McGilvery et al. |
| 2011/0054343 A1 | 3/2011 | Chetham et al. |
| 2011/0129129 A1* | 6/2011 | Avinash ............... A61B 5/4076 382/128 |
| 2012/0310055 A1* | 12/2012 | Jean .................. A61B 5/14532 600/310 |
| 2013/0223709 A1* | 8/2013 | Wagner ................ A61B 5/0036 382/128 |
| 2014/0081665 A1* | 3/2014 | Holmes .................. G16H 10/60 705/3 |

OTHER PUBLICATIONS

International Preliminary Report on Patentability dated Aug. 21, 2018 for Application No. PCT/AU2017/050127.

* cited by examiner

BODY STATE CLASSIFICATION

RELATED APPLICATIONS

This application is a U.S. National Phase under 35 U.S.C. 371 of the International Patent Application No. PCT/AU2017/050127, filed Feb. 15, 2017, and published in English on Aug. 24, 2017 as WO 2017/139838, which claims the benefit of U.S. Provisional Application No. 62/380,236, filed Aug. 26, 2016, and U.S. Provisional Application No. 62/295,971, filed Feb. 16, 2016, all of which are incorporated by reference in their entirety.

BACKGROUND OF THE INVENTION

The present invention relates to a method and system for use in determining reference ranges for use in assisting diagnosis of a body state in a biological subject, as well as a method and system for use in assisting diagnosis of a body state in a biological subject.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Vital signs are often used as a measure of the general physical health of an individual, with deviation from understood normal values being indicative of adverse health. The normal ranges for a person's vital signs typically vary depending on physical characteristics, such as age, weight, and sex.

There are currently four primary vital signs, namely body temperature, blood pressure, pulse (heart rate), and breathing rate (respiratory rate), often notated as BT, BP, HR, and RR. Scores have been proposed that combine the individual values of vital signs into a single numerical value, with the total being used as an indicator of general health.

However, the use of the four vital signs is typically of only limited use as it is generally only broadly indicative of health issues, without providing much guidance regarding particular body states. Additionally, there tends to be significant natural variation in these signs depending on factors such as general fitness and recent exercise. Consequently, measurement of vital signs is typically only broadly useful as a general guide of general health status.

It is known to perform impedance measurements in order to determine aspects of a subject's body or composition, such as the Fat-Free Mass, Fat Mass or the like. Additionally, it is known to perform impedance measurements for the specific purpose of identifying a body state, such as the presence or absence of lymphedema. An example of this is described for example in WO2008/138062, which describes a method for use in analysing impedance measurements performed on a subject, the method including, in a processing system determining at least one impedance value, representing the impedance of at least a segment of the subject, determining an indicator indicative of a subject parameter using the at least one impedance value and a reference and displaying a representation of the indicator.

However, impedance measurements are typically only used in specific contexts, such as performing body composition measurements, or performing targeted assessment of specific health conditions, such as lymphedema. Part of the reason for this is due to a high degree of variability in impedance measurements between individuals, meaning measurements are often specific to individuals.

Attempts to account for variability between patients have typically relied on limited studies. For example, many forms of impedance analysis are performed on the basis of data collected from a study of army personnel data as described for example in U.S. Army Natick Research, Development and Engineering Centre 1989 "Anthropometric Survey of U.S. Army Personnel: Summary Statistics Interim Report" Natick/TR89/027. However this data tends to be representative of a very small subset of the world's population and as such tends to make an analysis of impedance measurements unreliable on the broader population.

SUMMARY OF THE PRESENT INVENTION

In one broad form an aspect of the present invention seeks to provide a system for determining a body state indicator for a biological subject, the system including: a number of measuring systems, each measuring system being capable of performing impedance measurements on a user and having: a measuring device including: at least one signal generator electrically connected to drive electrodes to apply a drive signal to a user; at least one sensor electrically connected to sense electrodes to measure a response signal in the user; a measuring device processor that at least in part: controls the at least one signal generator; receives an indication of a measured response signal from the at least one sensor; and, generates measurement data indicative of at least one measured impedance value; and, a client device in communication with the measuring device, wherein the client device: receives the measurement data; generates user data indicative of the measurement data and a user identifier associated with the user; and, communicates the user data via a communication network; one or more one processing devices that: generate reference signatures by: obtaining user data for a plurality of reference individuals from one or more of the number of measuring systems, via the communications network; determines for each reference individual, at least in part using respective user data, reference data including: at least one reference impedance indicator obtained from user data by performing at least one impedance measurement on the reference individual; a reference body state indication indicative of any body states associated with the reference individual; and, reference characteristic data indicative of one or more physical characteristics of the reference individual; and, analyses the reference data for the plurality of reference individuals to establish the one or more reference signatures, each reference signature being indicative of at least one reference impedance indicator associated with a respective body state for respective physical characteristics; analyse impedance measurements for a subject by: obtaining user data for the subject from one of the number of measuring systems, via the communications network; determining, at least in part using the user data for the subject: subject characteristic data indicative of one or more physical characteristics of the subject; and, at least one subject impedance indicator derived from at least one measured impedance value for the subject; and, analysing the at least one subject impedance indicator at least in part using the reference signatures and the subject characteristic data; and, generating at least one body state indicator in accordance with the analysis.

Typically the reference impedance indicators include at least one of: at least one impedance value measured for at least one body segment of the reference individual; at least one impedance parameter value derived from at least one impedance value measured for at least one body segment of the reference individual; a fluid level indicator indicative of fluid levels in at least one body segment of the reference individual, the fluid level indicator being derived from at least one impedance value measured for at least one body segment of the reference individual.

Typically each reference signature includes a reference range based on a distribution of reference impedance indicators associated with reference individuals having a respective body state and respective physical characteristics.

Typically the one or more processing devices analyse the at least one subject impedance indicator by: selecting one or more of the reference signatures using the subject characteristic data; generating at least one subject signature indicative of the at least one subject impedance indicator; and, comparing the at least one subject signature to the selected reference signatures.

Typically the one or more processing devices: generate reference signatures by: determining at least one other reference body parameter value obtained by performing at least one measurement on one or more other body parameters of the reference individual; and, generating each reference signature so that each reference signature is indicative of at least one reference impedance indicator and at least one other reference body parameter value associated with a respective body state for respective physical characteristics and generate a subject signature by: determining at least one other subject body parameter value obtained by performing at least one measurement on one or more other body parameters of the subject; generating the at least one subject signature using the at least one other subject body parameter value.

Typically the at least one other reference body parameter value is indicative of at least one of: a body parameter value; a weight; a cardiac parameter value; a respiratory parameter value; a blood potassium level; a temperature; a blood pressure; a respiratory rate; a heart rate; and, a blood oxygenation level.

Typically the one or more processing devices retrieve medical record data from one or more electronic medical records, the medical record data including at least one of: subject characteristic data; at least one other subject body parameter value; reference characteristic data; at least one other reference body parameter value; and, a reference body state indication.

Typically the one or more processing devices retrieve medical record data using at least one of: a user identifier of a subject; a user identifier of a reference individual; and, a medical record identifier related to a user identifier.

Typically the one or more processing devices: determine a user identifier from the user data; retrieve a medical record identifier from an index using the user identifier; generate a query using the medical record identifier; transfer the query to an electronic medical record system; and, receive medical record data in response to the query.

Typically the one or more processing devices receive from the measuring device at least one of: subject characteristic data; at least one other subject body parameter value; reference characteristic data; at least one other reference body parameter value; and, a reference body state indication.

Typically the one or more processing devices, at least one of: store the at least one body state indicator; store the at least one body state indicator as part of an electronic medical record; provide an indication of the at least one body state indicator to the client device of a respective measuring system for display; and, provide an indication of the at least one body state indicator to a client device of a nominated party for display.

Typically the characteristic data includes at least one of: environmental characteristics associated with the reference individual, the environmental characteristics including at least one of: a location; an altitude; a temperature; and a humidity. physical characteristics including at least one of: a height; a weight; an age; a sex; an ethnicity; and, physical dimensions of at least one body segment of the reference individual.

Typically the measuring device includes at least one of: a first housing including spaced pairs of foot drive and sense electrodes provided in electrical contact with feet of the subject in use; and, a second housing including spaced pairs of hand drive and sense electrodes provided in electrical contact with hands of the subject in use.

Typically the client device is at least one of: a smart phone; and, a tablet.

In one broad form an aspect of the present invention seeks to provide a method for determining a body state indicator for a biological subject, the method including: providing a number of measuring systems, each measuring system being capable of performing impedance measurements on a user and having: a measuring device including: at least one signal generator electrically connected to drive electrodes to apply a drive signal to a user; at least one sensor electrically connected to sense electrodes to measure a response signal in the user; a measuring device processor that at least in part: controls the at least one signal generator; receives an indication of a measured response signal from the at least one sensor; and, generates measurement data indicative of at least one measured impedance value; and, a client device in communication with the measuring device, wherein the client device: receives the measurement data; generates user data indicative of the measurement data and a user identifier associated with the user; and, communicates the user data via a communication network; using one or more one processing devices to: generate reference signatures by: obtaining user data for a plurality of reference individuals from one or more of the number of measuring systems, via the communications network; determining for each reference individual, at least in part using respective user data, reference data including: at least one reference impedance indicator obtained from user data by performing at least one impedance measurement on the reference individual; a reference body state indication indicative of any body states associated with the reference individual; and, reference characteristic data indicative of one or more physical characteristics of the reference individual; and, analyses the reference data for the plurality of reference individuals to establish the one or more reference signatures, each reference signature being indicative of at least one reference impedance indicator associated with a respective body state for respective physical characteristics; analyse impedance measurements for a subject by: obtaining user data for the subject from one of the number of measuring systems, via the communications network; determining, at least in part using the user data for the subject: subject characteristic data indicative of one or more physical characteristics of the subject; and, at least one subject impedance indicator derived from at least one measured impedance value for the subject; and, analysing the at least one subject impedance indicator at least in part using the reference signatures and the subject characteristic data; and, generate at least one body state indicator in accordance with the analysis.

In one broad form an aspect of the invention seeks to provide a system for determining reference signatures for use in assisting identification of a body state in a biological subject, the system including at least one processing device that: obtains reference data for each of a plurality of reference individuals, the reference data including: at least one reference impedance indicator obtained by performing at least one impedance measurement on the reference individual; a body state indication indicative of any body states associated with the reference individual; and, characteristic data indicative of one or more physical characteristics of the reference individual; and, analyses the reference data to establish one or more reference signatures, each reference signature being indicative of at least one reference impedance indicator associated with a respective body state for respective physical characteristics.

In one broad form an aspect of the invention seeks to provide a method for determining reference signatures for use in assisting identification of a body state in a biological subject, the method including, in at least one processing device: obtaining reference data for each of a plurality of reference individuals, the reference data including: at least one reference impedance indicator obtained by performing at least one impedance measurement on the reference individual; a body state indication indicative of any body states associated with the reference individual; and, characteristic data indicative of one or more physical characteristics of the reference individual; and, analysing the reference data to establish one or more reference signatures, each reference signature being indicative of at least one reference impedance indicator associated with a respective body state for at least one of: respective physical characteristics; and, respective environmental characteristics.

In one broad form an aspect of the invention seeks to provide a system for use in assisting identification of a body state in a biological subject, wherein the system includes at least one processing device: determining subject data for the biological subject, the subject data including: at least one subject impedance indicator obtained by performing at least one impedance measurement on the subject; and, subject characteristic data indicative of one or more physical characteristics of the subject; and, using the subject data and reference signatures to generate a body state indicator, each reference signature being indicative of at least impedance indicators associated with a respective body state for respective physical characteristics, and the body state indicator being at least partially indicative of a likelihood of the subject having a respective body state.

In one broad form an aspect of the invention seeks to provide a method for use in assisting identification of a body state in a biological subject, wherein the method includes, in at least one processing device: determining subject data for the biological subject, the subject data including: at least one subject impedance indicator obtained by performing at least one impedance measurement on the subject; and, subject characteristic data indicative of one or more physical characteristics of the subject; and, using the subject data and reference signatures to generate a body state indicator, each reference signature being indicative of at least impedance indicators associated with a respective body state for respective physical characteristics, and the body state indicator being at least partially indicative of a likelihood of the subject having a respective body state. In one broad form an aspect of the invention seeks to provide a method for determining reference signatures for use in assisting identification of a body state in a biological subject, the method including: obtaining, from a number of sources, reference data for each of a plurality of reference individuals, the reference data including: at least one reference impedance indicator obtained by performing at least one impedance measurement on the reference individual; a body state indication indicative of any body states associated with the reference individual; and, characteristic data indicative of one or more physical characteristics of the reference individual; and, aggregating the reference data from the plurality of sources; mining the aggregated data to determine reference signatures indicative of at least one or more reference impedance indicators associated with a respective body state for at least one of: respective physical characteristics; and, respective environmental characteristics.

In one broad form an aspect of the invention seeks to provide a method for determining a body state indicator for a biological subject, the method including: obtaining at least one subject impedance indicator by performing at least one impedance measurement on the subject; and, using the at least one subject impedance indicator and subject characteristic data indicative of one or more physical characteristics of the subject to determine a body state indicator at least partially indicative of a likelihood of the subject having a respective body state by: comparing the at least one subject impedance indicators to one or more reference signatures, each reference signature being indicative of at least one impedance indicator associated with a respective body state for respective physical characteristics; and, generating the body state indicator at least partially based on a degree of similarity between the at least one subject impedance indicator and the reference signatures.

In one broad form an aspect of the invention seeks to provide a method for determining a body state indicator for a biological subject, the method including: obtaining body parameter values including: at least one subject impedance indicator obtained by performing at least one impedance measurement on the subject; and, at least one other body parameter value obtained by performing at least one measurement of at least one other vital sign of the subject, the at least one other vital sign being at least one of: a vital signs indicator; a cardiac parameter value; a respiratory parameter value; a blood potassium level; a fitness parameter; a temperature; a blood pressure; a respiratory rate; a heart rate; and, a blood oxygenation level; using the body parameter values and subject characteristic data indicative of one or more physical characteristics of the subject to determine a body state indicator at least partially indicative of a likelihood of the subject having a respective body state by: comparing the body parameter values to one or more reference signatures, each reference signature being indicative of body parameter values associated with a respective body state for respective physical characteristics; and, generating the body state indicator at least partially based on results of the comparison.

Typically the reference impedance indicators include at least one of: at least one impedance value measured for at least one body segment of the reference individual; at least one impedance parameter value derived from at least one impedance value measured for at least one body segment of the reference individual; a fluid level indicator indicative of fluid levels in at least one body segment of the reference individual, the fluid level indicator being derived from at least one impedance value measured for at least one body segment of the reference individual.

Typically the reference impedance indicators are obtained for at least some of the reference individuals, at least one of: for each of a plurality of body segments; at a number of different times; and, repeatedly over a time period.

Typically at least one reference impedance indicator is one of a number of reference body parameter values, the reference data further including at least one other reference body parameter value obtained by performing at least one measurement on one or more other vital signs of the reference individual, and wherein each reference signature is indicative of at least one reference impedance indicator and at least one other reference vital sign indicator associated with a respective body state for respective physical characteristics.

Typically the at least one other reference body parameter value is indicative of at least one of: a vital signs indicator; a cardiac parameter value; a respiratory parameter value; a blood potassium level; a fitness parameter; a temperature; a blood pressure; a respiratory rate; a heart rate; and, a blood oxygenation level.

Typically the characteristic data is indicative of environmental characteristics associated with the reference individual, the environmental characteristics including at least one of: a location; an altitude; a temperature; and a humidity.

Typically the at least one processing device: determines at least one body state group, the body state group being a group of reference individuals having a respective body state; and, determines at least one reference signature for each body state group using at least the reference impedance indicators of the reference individuals within the body state group.

Typically the at least one processing device: determines a plurality of characteristic groups, each characteristic group being a group of reference individuals having common characteristics; and, determines at least one reference signature for each characteristic group using at least the reference impedance indicators of the reference individuals within the characteristic group.

Typically the at least one processing device determines a plurality of characteristic groups within each of a number of body state groups.

Typically the at least one processing device determines a reference signature for each group based on at least a distribution of reference impedance indicators of the reference individuals within the group.

Typically the at least one processing device further determines the reference signature for a group based on a distribution of other body parameter values.

Typically each reference signature includes a reference range based on a distribution of reference impedance indicators associated with reference individuals having a respective body state and respective physical characteristics.

Typically each reference signature is based on at least one of: reference impedance indicators measured for respective body segments of the reference individuals; differences between reference impedance indicators measured for respective body segments of the reference individuals; changes in reference impedance indicators measured over time.

Typically each reference signature includes a plurality of reference ranges, each reference range being based on at least one of: a distribution of reference impedance indicators measured for a respective body segment; a distribution of differences in reference impedance indicators measured for different respective body segments; and, a distribution of impedance indicators measured at a specific times.

Typically each reference signature is indicative of relative differences in reference impedance indicators for respective body segments of reference individuals having a respective body state and respective, physical characteristics.

Typically the physical characteristics include at least one of: a height; a weight; an age; a sex; an ethnicity; and, physical dimensions of at least one body segment of the reference individual.

Typically the body state is at least one of: healthy; unhealthy; abnormal hydration; a fitness state; a disease state including a presence, absence or degree of at least one of: cancer; heart failure; congestive heart failure; oedema; and, lymphodema.

Typically at least some of the impedance measurements are performed as part of at least one of: a body composition measurement procedure performed on a plurality of reference individuals; and, a health check procedure performed on a plurality of reference individuals.

Typically at least some of the reference data is established in respect of healthy reference individuals and is used to establish a reference signature for at least one body state other than a healthy state.

Typically the system includes a number of measuring systems, each measuring system being configured to: determine at least part of the reference data for at least one reference individual; and, provide the at least part of the reference data to the at least one processing device via a communications network.

Typically each measuring system includes: an impedance measuring unit configured to perform impedance measurements; and, a processing system configured to provide the at least part of the reference data to the at least one processing device.

Typically each measuring system includes an impedance measuring unit, the impedance measuring unit including: at least one signal generator coupled to first electrodes provided in electrical contact with the subject in use, the at least one signal generator being adapted to generate a drive signal; at least one sensor coupled to second electrodes provided in electrical contact with the subject in use, the at least one sensor being adapted to measure a response signal; and, a measuring device processor that at least in part controls the at least one signal generator and receives an indication of a measured response signal from the at least one sensor, allowing the at least one impedance measurement to be performed.

Typically the impedance measuring unit includes: a measuring device including: the at least one signal generator; the at least one sensor; the measuring device processor; and, a first connector electrically connected to the at least one sensor and the at least one signal generator; and, a connectivity module including: the electrodes; and, a second connector electrically connected to the electrodes, wherein in use the measuring device is connected to the connectivity module by interconnecting the first and second connectors so that first electrodes are electrically connected to the at least one signal generator and a second electrodes are electrically connected to the at least one sensor, thereby allowing the drive signal to be applied to the reference individual via the first electrodes and allowing the response signal to be measured via the second electrodes so that the at least one impedance measurement can be performed.

Typically the measuring device is adapted to be used with a number of different connectivity module types, and wherein the measuring device processor performs the at least one impedance measurement at least in part depending on the connectivity module type of a connected connectivity module.

Typically each measuring system includes a processing system that: causes impedance measurements to be performed by the measuring unit; and, determines the body state indication and characteristic data.

Typically the processing system: determines an impedance measurement process to be performed, the impedance measurement process including a sequence of impedance measurements; causes the measuring unit to perform the sequence of impedance measurements; receives an indication of at least one impedance value from the measuring unit, the at least one impedance value being indicative of a measured impedance; and, generates impedance data using the at least one impedance value.

Typically the impedance data includes at least one of: at least one impedance indicator; and, at least one impedance value.

Typically the processing system determines the body state indication at least one of: in accordance with input commands; in accordance with an indication of a body state confirmed by a clinician; by retrieving an indication of a body state from a database; and, by retrieving an indication of a body state from a medical record.

Typically the processing system determines the characteristic data at least one of: in accordance with input commands; by retrieving an indication of a physical characteristics; and, using at least one physical characteristic sensor.

Typically each measuring system includes at least one physical characteristic sensor that senses at least one of: at least one physical characteristic of the reference individual; and, at least one environment characteristic sensor that senses at least one environment characteristic relevant to the reference individual.

Typically the physical characteristic sensor includes an imaging device that captures at least one image of the reference individual and wherein the characteristic data is derived at least in part from the at least one image.

Typically the processing system: uses the at least one image to determine at least one of a silhouette and a three dimensional model of the reference individual the reference individual; and, derives the physical characteristics from the at least one of a silhouette and a three dimensional model of the reference individual.

Typically the processing system: determines physical dimensions for at least part of at least one segment of the reference individual; uses the physical dimensions to determine a shape factor at least partially indicative of a shape of the at least one segment; calculates a fluid indicator indicative of the fluid levels in the segment at least in part using the at least one impedance value and the shape factor.

Typically the fluid level indicator is a body composition indicator.

Typically the physical dimensions include a length and circumference of the at least one segment.

Typically the physical dimensions are at least one of: measured for the reference individual; and, derived from characteristic data measured for the reference individual.

Typically the system is for use in assisting identification of a body state in a biological subject and wherein the at least one processing device: determines subject data for the biological subject, the subject data including: at least one subject impedance indicator obtained by performing at least one impedance measurement on the subject; and, subject characteristic data indicative of one or more physical characteristics of the subject; and, uses the subject data and the reference signatures to generate a body state indicator, the body state indicator being at least partially indicative of a likelihood of the subject having a respective body state.

Typically the subject impedance indicators include at least one of: at least one impedance value measured for at least one body segment of the subject; at least one impedance parameter value derived from at least one impedance value measured for at least one body segment of the subject; a fluid level indicator indicative of fluid levels in at least one body segment of the subject, the fluid level indicator being derived from at least one impedance value measured for at least one body segment of the subject.

Typically the subject impedance indicators are obtained at least one of: for each of a plurality of body segments; at a number of different times; and, repeatedly over a time period.

Typically at least one subject impedance indicator is one of a number of subject body parameter values, the subject data further including at least one other subject body parameter value obtained by performing at least one measurement on one or more other body parameters of the subject.

Typically the at least one other subject body parameter value is indicative of at least one of: a vital signs indicator; a cardiac parameter value; a respiratory parameter value; a blood potassium level; a fitness parameter; a temperature; a blood pressure; a respiratory rate; a heart rate; and, a blood oxygenation level.

Typically the characteristic data is indicative of environmental characteristics associated with the subject, the environmental characteristics including at least one of: a location; an altitude; a temperature; and a humidity.

Typically the at least one processing device receives subject data from a measurement system via a communications network.

Typically the at least one processing device: uses the subject data to identify one or more of the reference signatures; and, generates the body state indicator at least partially in accordance with the identified one or more reference signatures.

Typically the at least one processing device: determines selected reference signatures using the subject characteristic data; compares at least the subject impedance indicators to the selected reference signatures; and, generates the body state indicator at least partially in accordance with results of the comparison.

Typically the at least one processing device: generates at least one subject signature indicative of the at least one subject impedance indicator and at least one other subject body parameter indicator; and, compares the at least one subject signature to the selected reference ranges.

Typically the at least one processing device generates the body state indicator based on a degree of similarity between the subject signature and the selected reference signatures.

Typically the body state indicator is indicative of a likelihood of the subject having at least one body state.

Typically the body state is at least one of the presence, absence and degree of one or more medical conditions.

Typically each reference signature represents a combination of reference body parameter values including at least one reference impedance indicator, the combination of reference body parameters being uniquely indicative of a respective body state for respective physical characteristics.

Typically the at least one processing device is part of a network architecture, and wherein the at least one processing device is configured to at least one of: analyse the reference data in the network architecture; store reference signatures in the network architecture; analyse subject data in the network architecture; and, provide reference signatures to a processing device via a communications network to allow the reference signatures to be used in analysing subject data.

Typically the method includes obtaining the reference data at least one of: during body composition measurements; during healthcare checks; and, during home monitoring.

Typically at least one reference impedance indicator is one of a number of reference body parameter values, the reference data further including at least one other reference body parameter value obtained by performing at least one measurement on one or more other body parameters of the reference individual, and wherein each reference signature is indicative of at least one reference impedance indicator and at least one other reference body parameter indicator associated with a respective body state for respective physical characteristics.

Typically the at least one other reference body parameter value is indicative of at least one of: a vital signs indicator; a cardiac parameter value; a respiratory parameter value; a blood potassium level; a fitness parameter; a temperature; a blood pressure; a respiratory rate; a heart rate; and, a blood oxygenation level.

It will be appreciated that aspects of the broad forms of the invention and their respective features can be used in conjunction, interchangeably and/or independently, and reference to separate broad forms is not intended to be limiting.

BRIEF DESCRIPTION OF THE DRAWINGS

An example of the present invention will now be described with reference to the accompanying drawings, in which:—

DETAILED DESCRIPTION OF THE PREFERRED EMBODIMENTS

Figure 1:
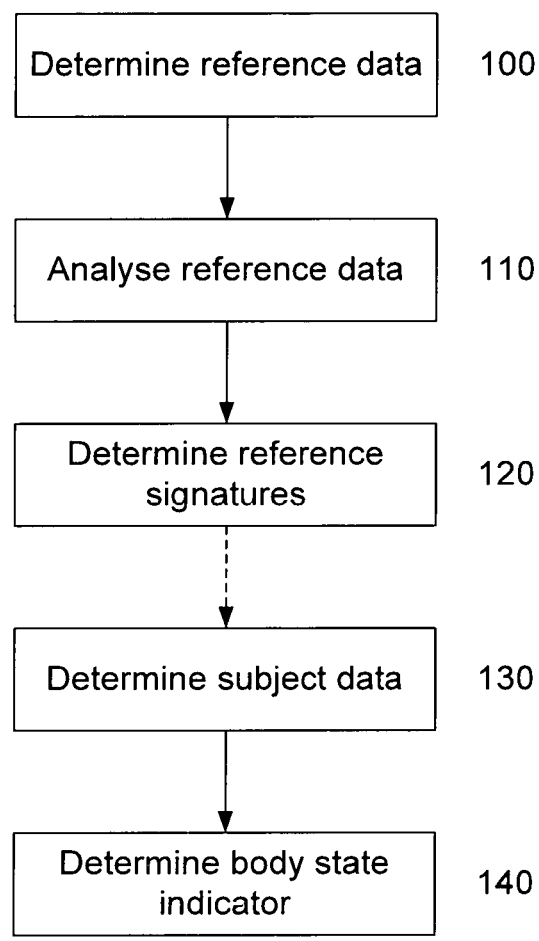
FIG. 1 is a flowchart of an example of a method for determining reference signatures and using the reference signatures to assist identification of a body state of a subject.
Figure 2:
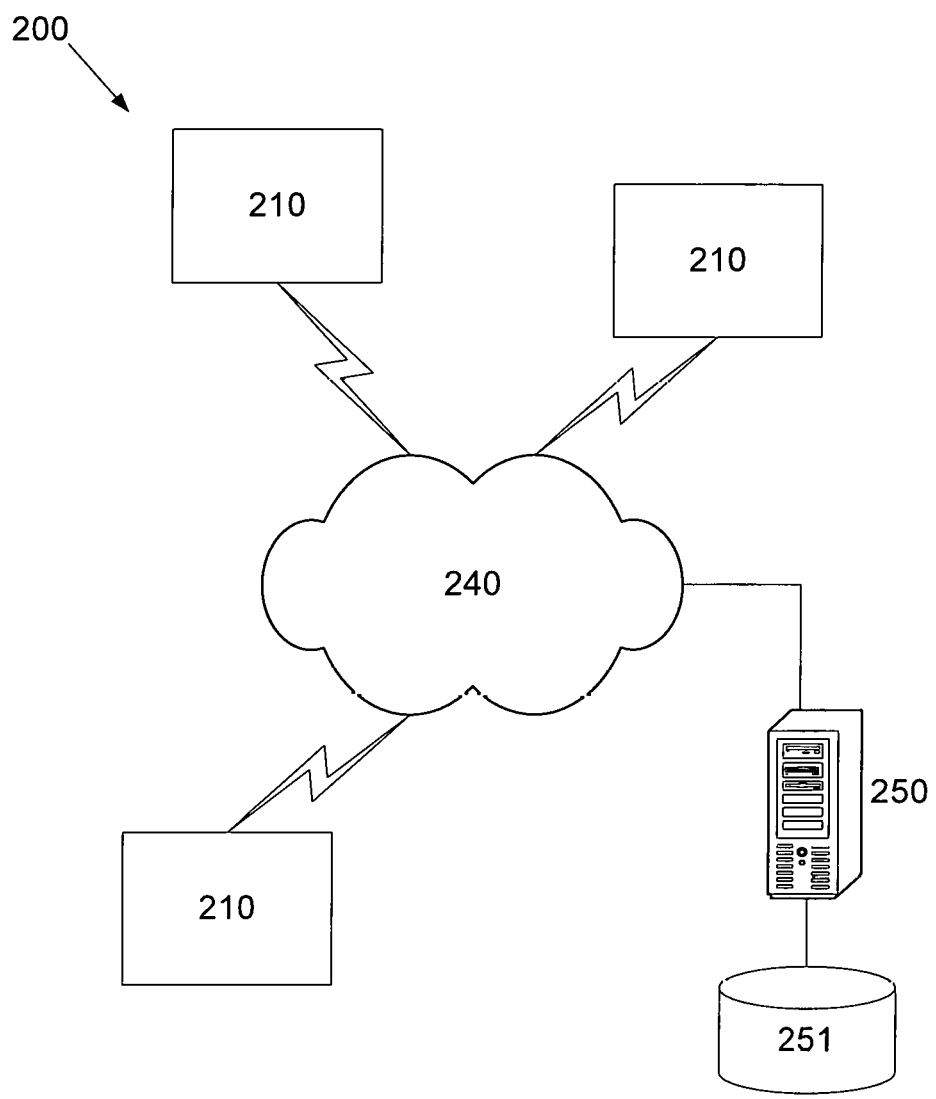
FIG. 2 is a schematic diagram of an example of a system for determining reference signatures and using the reference signatures to assist identification of a body state of a subject.

An example of a method for determining reference signatures for use in assisting identification of a body state in a biological subject and for further performing identification of a body state in a biological subject using the reference signatures will now be described with reference to FIG. 1.

For the purpose of illustration, it is assumed that the process is performed at least in part using one or more electronic processing devices forming part of one or more processing systems, such as servers, which are in turn connected to one or more measuring systems, such as impedance measuring systems or the like, via a network architecture. In one example, this is performed at least using a cloud based architecture that interfaces with measuring systems or other client devices located at multiple locations, as will be described in more detail below.

For the purpose of explanation, the term "reference individual" is used to refer to one or more individuals in a sample population, with "reference data" being used to refer to data collected from the reference individuals. The term "subject" refers to any individual that is being assessed for the purpose of identifying a body state, with "subject data" being used to refer to data collected from the subject. The reference individuals and subjects are animals, and more particularly humans, although this is not intended to be limiting and the techniques could be applied more broadly to other vertebrates and mammals.

The term "body state" will be understood to include a disease state and/or wellness state of a subject. In particular, a disease state is typically, a presence, absence, degree, severity or prognosis associated with a respective medical condition, whilst a wellness state could include an indication of a general level of health and/or fitness, as well as specific indicators of heath and/or fitness.

In this example, at step 100 reference data is obtained for each of a plurality of reference individuals. The reference data includes at least one reference impedance indicator obtained by performing at least one impedance measurement on a reference individual, a body state indication indicative of any body state associated with the reference individual and characteristic data indicative of one or more physical characteristics of the reference individual and/or environmental characteristics relevant to the individual.

The reference data could be obtained in any appropriate manner depending on the preferred implementation. For example, impedance indicators could be determined by performing impedance measurements, receiving data from an impedance measuring device, retrieving details of previously performed impedance measurements or the like. The indicators could be values of measured impedances and/or could be values derived therefrom, such as impedance parameter values, fluid level indicators, or the like. In one example, the impedance indicators are used in a manner akin to a vital sign to be indicative of the individual's health status and could be determined in conjunction with body parameter values, such as other vital sign indicators or values, as will be described in more detail below.

The indication of a body state could be an indication of any disease or condition suffered by the individual, including a healthy state or specific medical condition, and could be determined in any appropriate manner. For example, this could be achieved by having a healthcare professional, such as a medical practitioner, perform a diagnosis of the individual and manually provide the information, by examining results of medical tests, retrieving details of a medical history, from a health record, or the like. The indication could simply identify a presence or absence of a body state, but more typically would include an indication of a degree or severity of the body state, such as a classification, a prognosis for the body state, or the like.

The body state indicator could be indicative of a specific condition, or could be a general indication of a measured body parameter value that is in turn indicative of a condition, such as one or more of Body Composition, Dry Lean Mass, Lean Body Mass, Skeletal Muscle Mass, Segmental Lean Analysis, Body Fat Mass, Segmental Fat Analysis, BMI (Body Mass Index), (Percent Body Fat), Visceral Fat Area, Visceral Fat Level, Total Body Water, Intracellular Water, Extracellular Water, ECW/TBW, Segmental Body Water, Segmental ECW/TBW, Segmental ICW Analysis, Segmental ECW Analysis, Body-Fat-LBM Control, BMR (Basal Metabolic Rate), Leg Lean Mass, TBW/LBM, Whole Body Phase Angle, Segmental Phase Angle, Reactance, Impedance of Each Segment per frequency, or Body Water Composition History. The body state could also be indicative of a general level of athletic fitness, such as whether the individual is fit or unfit.

Similarly, the characteristic data is typically indicative of physical characteristics, such as the individual's age, weight, height, sex, ethnicity, or physical dimensions of one or more body segments, or any other relevant information and could be measured, either manually or using appropriate measuring devices, or provided to the processing device or retrieved from records of previous measurements. Additionally, characteristic data could include any other attribute associated with the individuals that could potentially have an impact on impedance measurements, such as details of any medication currently being taken by the individual or the like.

The reference data may also include other sensed data, include but not limited to other measured body parameter values, such as values of cardiac or respiratory parameters, body parameter values, fitness parameters, environmental characteristics relevant to the individual, or the measurement environment, or the like, as will be described in more detail below.

At step 110, the at least one processing device analyses the reference data to establish one or more reference signatures at step 120. Each reference signature is indicative of at least impedance indicators, and optionally other body parameter values, associated with respective body states for respective physical characteristics.

In one example, each reference signature represents a distribution of impedance and optionally other body parameter values, such as body parameter values, which can be used to indicate the likelihood of a subject having a respective condition. In order to achieve this, it is typical to derive a reference signature for each condition for a respective set of characteristics, so that multiple reference signatures are defined for each of a number of body states. Thus a respective signature can be developed for a respective body state, or combination of multiple body states, for a respective set of characteristics. Reference signatures can also be derived for combinations of multiple conditions for example in the event that the individual is co-morbid or poly-morbid, as well as to take into account other sensed parameters, such as environmental characteristics, or the like, as will be described in more detail below. Thus, a signature could be developed for people with heart failure, and a different signature developed for people with both heart failure and cancer.

Once reference signatures have been established, these can then be used to determine a body state indicator indicative of any body states associated with a subject. In order to achieve this, at step 130 the processing device determines subject data for the subject, the subject data including at least one subject impedance indicator obtained by performing at least one impedance measurement on the subject and subject characteristic data indicative of one or more physical characteristics of the subject and/or environmental characteristics relevant to the subject. The subject data may also optionally include other body parameter values, as will be described in more detail below.

Again the impedance indicator and subject data can be obtained in any suitable manner and could be measured, input manually, received from a remote source, retrieved from previously performed measurements stored in a database, or the like.

At step 140 the subject data and the reference signatures are used to determine a body state indicator. This is typically achieved by comparing the subject data to the reference signatures, and in particular reference signatures established for individuals having similar physical characteristics to the subject, and then assessing the likelihood of the subject having a body state based on the similarity of the impedance indicators to those associated with each reference signature. This allow a body state indicator to be generated, the body state indicator being at least partially indicative of the likelihood of the subject having a respective body state.

Accordingly, the above described process utilises impedance measurements to determine body state indicators, which can be used in identifying body states in subjects. This allows impedance indicators obtained from impedance measurements to be used in a manner akin to other vital signs measurement, allowing these to be used as a first point of reference for clinicians when making a diagnosis.

Whilst using impedance measurements as a vital sign could be achieved in other ways, the above approach involves collecting reference data from a number of reference individuals, and then using this to establish reference signatures. In particular, establishing reference signatures, such as reference ranges, for different physical characteristics, allows these to be taken into account when measurements are analysed so that the impedance measurements can be interpreted in a meaningful manner. In particular this allows the natural variations between members of a population that arise due to different physical characteristics to be taken into account, so that the assessment is relevant to the particular subject under consideration.

In a broad form, this approach can be used to allow reference signatures to be derived corresponding to healthy individuals, so that as a coarse measure, this can be used to identify whether a subject is healthy or unhealthy. However, more preferably reference signatures can be derived for specific body states, such as heart failure, cancer, or the like, allowing specific medical conditions to be more easily identifier.

In this regard, as fluid levels within the body react differently to different conditions, and in particular can demonstrate a greater degree of variation that other more traditional vital signs, this approach has the ability to offer a greater discriminatory ability than traditional vital signs.

For example, over hydration could result in a general body wide increase in fluid levels, whereas medical conditions such as heart failure can lead to pooling of fluids in specific body segments, meaning impedance measurements alone can distinguish between these conditions. Accordingly, this allows for reference signatures to be derived which are specific to respective conditions, allowing the impedance indicators to be used in identifying specific body states, and not just making a healthy/unhealthy discrimination.

It will further be appreciated that whilst impedance measurements could be used independently of other body parameters, they could also be used in conjunction with other body parameters, such as other vital signs, to further improve diagnostic ability. For example, considering fluid levels in conjunction with pulse, breathing rate, temperature and/or blood pressure, can assist in distinguishing heart failure from other conditions that might also lead to pooling of blood, such as venous insufficiency. Thus, using impedance measurements as a further vital sign in addition to other vital signs can further assist clinicians in distinguishing between different body states.

Furthermore, impedance measurements can be used to serve a variety of purposes, allowing reference data to be collected during common day-to-day procedures, such as general health checks, body composition measurements, fitness assessments, or the like. Additionally, by virtue of their inherent nature, impedance measurements are typically performed electronically in a reasonably standardised manner. Thus, measurements may be performed on individuals in scenarios absent of any particular clinical significance, and without medical training, for example in a manner similar to daily weight measurements. This in turn allows a sufficiently large volume of reference data to be statistically significant, in particular allowing impedance indicators to be measured for a wide range of physical characteristics, so that respective signatures can be derived for multiple defined sets of characteristics, making the assessment more accurate than would otherwise be the case.

For example, such measurements can be performed readily on any individual using straightforward body composition measuring devices, and without requiring specialist medical intervention. This enables a large volume of reference data to be readily collected, allowing this to be leveraged to establish reference signatures which can be used in diagnosing body states for which collection of data might otherwise be problematic.

Thus, it will be appreciated that if impedance measurements are performed as part of a general health check, in a manner akin to which blood pressure checks are performed, the impedance measurements, together with information regarding the individual's general health status, such as measures of other body parameters, an identification of any body states or details of the relevant individual's medical history, can be provided allowing in depth reference signatures to be established which are both indicative of healthy individuals, but which are also indicative of other body states some of the individuals may have including, hut not limited to healthy, unhealthy, a hydration state, such as normal hydration, abnormal hydration, over hydration or dehydration, a fitness state, such as fit, very fit, unfit, very unfit, a disease state such as a presence, absence or degree of cancer, heart failure, congestive heart failure, oedema, lymph oedema or any other diagnosable condition. Additionally, reference data could also be collected by having individuals perform body composition analysis outside of a clinical setting, for example in the home, and then using information collected from medical records, fitness measuring devices, or the like, to then form the reference data.

It will be appreciated from this that the impedance indicators, body state indicator(s) and physical characteristic information could be established separately or otherwise obtained from multiple independent sources, and then combined as required in order to create the reference data. For example, this allows information from electronic medical records or other similar sources to be retrieved and combined with data derived from measurements performed using an impedance measuring device.

In any event, the above approach allows reference data to be collected from multiple different sources, and processed centrally, for example in a cloud based environment. This approach to reference data collection ensures generated reference signatures are based on reference data collected for a wider subset of the population than would otherwise be possible if measurements were performed in respect of targeted conditions. In particular, this allows reference data to be collected from individuals having a wide range of different physical characteristics and for a wide variety of different body states. Collecting, aggregating and then processing the reference data centrally in this manner allows signatures to be derived that are unique to particular conditions for a respective set of physical and/or environmental characteristics, making such reference signatures more reliable and thereby improving the diagnostic ability associated with impedance measurement processes for a range of different body states.

Accordingly, the above described approach leverages the use of impedance indicators as a potential biomarker for different body states, as well as indicators of body composition, to allow a high volume of impedance data to be collected. Aggregating and then mining this data, together with information regarding physical and/or environmental characteristics and known body states, allows correlations or other relationships to be determined between particular impedance indicators, and optionally other body parameters, and certain body states. These relationships can be embodied as reference signatures, allowing for impedance measurements to be analysed together with other pertinent information in a substantially automated fashion to generate body state indicators indicative of one or more body states for a subject. It will therefore be appreciated that this can lead to a significant improvement in the ability to perform rapid and quantified body state identification.

Furthermore, having performed measurements for a subject allowing body states to be identified, ongoing monitoring can be performed to track ongoing progression of a body state, in a manner similar to ongoing monitoring of other vital signs, such as blood pressure or the like. Thus, for example, impedance indications measured initially can be used to establish a subject specific baseline reference signature, with changes relative to the subject specific baseline acting as an indicator of changes in the body state. Thus, in this instance, the reference signature is established for the subject to define a baseline.

This is particularly important for chronic conditions, such as heart failure, which represent a significant burden on the economy. Typically in existing cases, patients are sent home and required to monitor vital signs such as respiratory capabilities, blood pressure, heart rate or the like, using this to judge whether further interventions are required. However, using impedance measurements as a further vital sign, can vastly improve the ability to track ongoing changes in the severity of the body state.

In particular, fluid level changes often occur in advance of other physical symptoms, such as changes in pulse or breathing rate, allowing the onset and progression of conditions to be more easily and more accurately tracked, even before changes in other physical symptoms are noticeable. Furthermore, different reference signatures could be developed to cover different states or degrees of severity of a single condition, allowing the process to be used in performing risk stratification, allowing subjects to be more easily categorised, in turn allowing ongoing patient monitoring and management to be more effectively performed. This can include identify and potential managing conditions at a pre-clinical stage, often avoiding or reducing the burden of involved long term intervention.

Furthermore, the inherent electronic nature of the measurement process allows measurements to be performed and analysed with minimal intervention, for example only requiring a user to grasp electrode or stand on a foot plate, and can result in impedance measurements providing an earlier and more reliable indicator of adverse body states. This can in turn provide an earlier indication of when intervention may be required, allowing this to be performed at a more appropriate time, and hence more cost effectively. As part of this, impedance measuring devices are typically capable of being used in the home environment, without medical expertise, meaning tracking of body state progression can be performed more reliably in a home environment. This can increase the frequency with which measurements are collected, resulting in intervention being sought in a more timely fashion. Additionally, this allows subjects to be presented with the result of the analysis and hence become more conscious of the current level of progression or severity of any condition. This can help the subject understand the impact of lifestyle, in turn helping ensure improved management outcomes.

A number of further features will now be described.

In one example, the reference impedance indicators include at least one impedance value measured for at least one body segment of the reference individual, at least one impedance parameter value derived from at least one impedance value measured for the at least one body segment of the reference individual or a fluid level indicator indicative of fluid levels in at least one body segment of the reference individual, the fluid level indicator being derived from at least one impedance value measured for at least one body segment of the reference individual.

Accordingly, it will be appreciated that reference signatures can be established directly based on impedance values, or based on impedance parameter values or fluid level indications derived from impedance values. Thus the impedance values could be measurements of impedance at one or more specific frequencies, with derived impedance parameter values corresponding to measurement of impedance at other frequencies, such as zero or infinite frequencies as will be appreciated by persons skilled in the art. Alternatively, the reference signatures could be based on fluid levels derived from impedance measurements, such as indications of extracellular fluid levels, intracellular fluid levels, or a ratio of the two.

Whilst typically a similar impedance indicator is used for all reference signatures, this is not essential and the indicator used could be selected to improve the diagnostic ability of the reference signature. For example, whilst a measure of extracellular fluid levels may be sufficient to diagnose some diseases such as congestive heart failure, other indicators, such as a ratio of extracellular to intracellular fluid may be required for other body states. Accordingly, in one example, the process of determining the reference signatures could include assess the effectiveness of different impedance indicators to distinguish between different body states.

The impedance measurements could be single frequency impedance measurements or could be performed at multiple frequencies as will be described in more detail below. The impedance measurements could be performed at any suitable frequency, but would typically include at least one low frequency measurement performed at less than 100 kHz and more typically about 30 kHz, and may also include one or more measurements at higher frequencies.

Additionally, reference impedance indicators could be obtained for each of a plurality of body segments, at a number of different times and repeatedly over a time period. This allows the reference signatures to be based not only on measurements for individual body segments, such as particular limbs, taken in isolation but allows these to take into account relative fluid levels in different parts of the body. For example, an increase in torso fluid levels only might be indicative of a different body state to an increase in fluid levels in the torso and other body segments. Accordingly, the reference signatures could be based on ratios of impedance indicators in different body segments, instead of or as well as absolute impedance indicators. The reference signatures could also be based on changes in impedance indicators over time, so that impedance indicators increasing/decreasing in value could be indicative of different body states and/or severities of body state. It will also be appreciated that fluid levels and hence impedance indicators are typically subject to variations based on a wide range of factors, such as diet and fluid intake, exercise, menstrual cycle or the like. Accordingly, impedance indicators could be measured at specific times, such as prior to or post exercise or eating, or the like. Thus, different signatures could be derived for measurements performed at different times of the week, or pre or post certain activities.

As previously mentioned, the impedance indicator could be used in conjunction with measures of other body parameters. In this case, the impedance indicator could be one of a number of reference body parameter values, with the reference data further including at least one other reference body parameter value obtained by performing at least one measurement on one or more other body parameters of the reference individual. In this case, each reference signature can be indicative of at least one reference impedance indicator and at least one other reference body parameter indicator associated with a respective body state for respective physical and/or environmental characteristics. Thus, the reference signature for a first condition could be a defined impedance value and high heart rate, whilst a different second condition could be characterised by the same impedance value with a lower heart rate. The ability to define reference signatures based on impedance indicators as well as other vital statistics allows for multi-dimensional reference signatures to be defined, providing further improved discriminatory capabilities.

Thus, the reference signatures can be based on indicator values for other body parameters. In this case, the other body parameters could be any body parameters, including but not limited to vital signs indicators, a cardiac parameter value, a respiratory parameter value, a blood potassium level, a fitness parameter, such as a number of steps walked, a temperature, a blood pressure, a respiratory rate, a heart rate and a blood oxygenation level.

The signature could also be based on environmental characteristics. For example, an ambient temperature, humidity or location could be used to further classify reference signatures, with subject signatures then being compared to reference signatures determined with similar environmental characteristics. This can take into account the fact that some conditions could be specific to certain environmental characteristics, so that certain medical conditions may not be prevalent in certain climates or certain locations. This can be useful in tracking disease outbreaks, as well as taking into climate, exposure to toxins or pollutants, or the like.

In generating the reference signatures, the processing device typically determines at least one body state group, the body state group being a group of reference individuals having a respective body state, and then determines at least one reference signature for each body state group using the impedance indicators of the reference individuals within the body state group. Accordingly, this process operates to segment the reference individuals into groups of individuals having certain body states, then establishing a respective reference signature for individuals within that group. The reference signature could therefore be a reference range based on a distribution of impedance indicators established for individuals within that group. In this way, if an impedance indicator is measured for a subject that falls outside the reference range, it is unlikely that that individual suffers from that particular body state.

Additionally, the processing device typically determines a plurality of characteristic groups, each characteristic group being a group of reference individuals having common physical characteristics. The processing device then determines at least one reference signature for each characteristic group using the impedance indicators of the reference individuals within the characteristic group. The characteristic groups are typically established as subgroups of the body state groups, so that each body state group is further divided into subgroups of individuals having respective physical characteristics. This allows the body state to be identified by comparing the subject data measured for a particular subject to reference signatures established for individuals having similar physical characteristics thereby increasing the reliability of this process. It will be appreciated that a similar process can be performed in respect of other measured parameters, such as environmental characteristics, location, or the like, allowing reference signatures to be established which are specific to particular ambient conditions or locations, with a comparison for a subject being performed relative to an equivalent signature group.

As mentioned above, the processing device can determine a reference signature for a group based on a distribution of impedance indicators of the reference individuals within the group. The distribution would typically follow a distribution curve, such as a Bell Curve or the like, with a comparison of a subject impedance indicator to the distribution allowing an indication of the likelihood of a subject suffering from a particular body state. Thus, this could be indicative of a probability of the subject having a respective condition.

It will be appreciated that in this instance, if signature includes reference ranges having multiple different impedance indicators and/or other vital signs distributions, equivalent measured values for the subject be compared to each of the distributions, which the result of each comparison being combined to provide an overall indication of the likelihood the subject has a particular body state.

The reference signature can include defined values for absolute and/or relative values of impedance indicators obtained from one or more body segments. Thus, each reference signature could be based on at least one of reference impedance indicators measured for respective body segments of the reference individuals, differences between reference impedance indicators measured for respective body segments of the reference individuals and changes in reference impedance indicators measured over time. The reference signature could also include threshold values of impedance indicators or ranges or thresholds of changes in absolute or relative impedance indicators measured over defined time periods. Thus, each reference signature could therefore include a plurality of reference ranges, each reference range being based on at least one of a distribution of reference impedance indicators measured for a respective body segment, a distribution of differences in reference impedance indicators measured for different respective body segments and a distribution of impedance indicators measured at a specific times.

In one example, the reference signatures could be in the form of a multi-dimensional vector, with each row in the vector being indicative of a value or range of values for a respective body parameter. In one example, a reference vector is generated for each reference individual, with clustering being performed to group reference vectors relating to common body states and physical characteristics, and thereby identify reference signatures. For example, this could be performed using iterative global partitioning clustering algorithms and Bayesian evidence classification, support vector machines, K-means classification, or the like, which can be used to effectively define decision boundaries in the multi-dimensional vector space, such that if a corresponding vector derived from the subject data falls within the decision boundary, this indicates that the subject has the respective condition.

As previously mentioned, impedance measurements for the reference individuals can be performed as part of a body composition measurement process, or general health check and accordingly at least some of the reference data is generally established at least in respect of healthy individuals. Despite this, the reference data can still be used to establish reference signatures for a body state. For example, if an individual falls outside a healthy reference signature, this is indicative that the individual has at least one potentially unknown body state. As reference data is collected from individuals with respective body states, this can then be further used to sub-classify a generally unknown body state into particular body states.

It will be appreciated from this that initial coarse ranges might be established with the ranges being refined over time as more reference data is collected. As part of this process, when measurements are performed on subjects to assist with body state identification, the collected subject data can be used as reference data, once any body states have been clinically confirmed. For example, if a subject is analysed and the body state indicator is indicative of heart failure, the subject can be examined by a medical practitioner to confirm if they have heart failure. In the event heart failure is confirmed, the subject impedance indicators can be added to the reference signature associated with heart failure.

Once reference ranges have been established, subject data can then be collected from subjects in a similar manner, and used to perform body state identification. Thus, subject data including subject impedance indicators and optional other subject body parameter values, together with physical characteristics, can be obtained and used in conjunction with the reference signatures determine a body state indicator.

It will be appreciated that the subject impedance indicators will be broadly similar to the reference impedance indicators described above and these will not therefore be described in further detail.

Having received the subject data, the processing device can use the subject data to determine a body state indicator indicative of a likely body state by using the subject data to identify one or more of the reference signatures, generating the body state indicator at least partially in accordance with the identified one or more reference signatures. This process typically includes determining selected reference signatures using the subject characteristic data, allowing the subject data to be compared to reference signatures established for reference individuals having similar characteristics to the subject. This accounts for variations in measured impedance or other vital sign values that might be inherent for individuals with different sets of physical characteristics. Following this, the subject data and in particular the impedance indicator is compared at least the subject impedance indicators to the selected reference signatures and generating the body state indicator at least partially in accordance with results of the comparison.

The comparison can be performed in any manner, and will for example depend on the nature of the reference. In one example, this process involves generating at least one subject signature indicative of the at least one subject impedance indicator and at least one other subject body parameter value and comparing the at least one subject signature to the selected reference ranges. For example, if the reference signature is a multidimensional vector, then a similar subject signature vector can be created and compared using a suitable analysis technique, such as a Bayesian classification scheme or the like. The processing device can then generate the body state indicator based on a degree of similarity between the subject signature and the selected reference signatures, with the body state indicator being indicative of a likelihood of the subject having at least one body state, for example based on the relative proximity of the subject signature and the reference signatures.

It will be appreciated that the body state indicator could be of any appropriate form, and could be indicative of a degree of similarity of the subject and reference signatures. Thus could include for example, determining a probability of the subject signature being a match to one or more of the reference signatures, and hence a probability of the subject having one or more different body states. Alternatively, this could simply select a most likely match and provide an indication of a body state on that basis.

It will be appreciated that the above described process can be performed on an ongoing basis, in order to monitor progression of a body state. For example, performing repeated measurements for the subject, for example on a day-to-day or weekly basis, allows progression of body states to be monitored. This in turn can significantly assist with long term management of chronic diseases.

For example, once diagnosed with chronic heart failure, a subject might repeat the measurement process in a home setting. In this instance, centralised analysis of the results can be used to identify if the subject's condition is worsening, in turn used to ensure early intervention is performed. For example, multiple different signatures can be established for different stages of progression of heart failure, allowing an assessment to be made as to a severity of the condition in the subject and/or a likely prognosis. This can also be used to track whether treatment is improving the condition.

In this regard, it will also be appreciated that initial readings for the subject can be used as a baseline, effectively acting as a personalised reference baseline signature, with variations from the baseline signature being used to assess changes in the condition. Additionally, ongoing comparison to the reference signatures can be used to understand the impact of variations from the baseline, in particular understanding the degree to which the condition or body state is worsening or improving, and whether any secondary body states are arising, which can in turn be used to guide ongoing treatment.

The above described process is typically implemented using a distributed architecture including a number of measuring systems in communication with one or more processing devices. In particular, each measuring system can be configured to determine at least part of the reference data for at least one reference individual and provide the at least part of the reference data to the at least one processing device via a communications network. Similarly, the measuring devices could be used to measure subject data when used in performing identification, as will be described in more detail below.

An example system will now be described with reference to FIGS. 2 to 5.

In this example, the system 200 includes a number of measuring systems 210 coupled via a communications network 240 to one or more other measuring systems 210 and/or one or more processing devices, such as a server 250, which may in turn be coupled to a database 251. This arrangement allows reference data and/or subject data to be collected by the measurement systems 210 and provided to the server 250 for analysis. Collected data may also be stored in the database 251 together with resulting reference signatures and/or body state indicators, allowing this information to be remotely accessed and viewed by third parties, such as clinicians, or the like.

In the above arrangement, the communications network 240 can be of any appropriate form, such as the Internet and/or a number of local area networks (LANs) and provides connectivity between the measuring systems 210 and the server 250. It will however be appreciated that this configuration is for the purpose of example only, and in practice the measuring systems 210 and server 250 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

Figure 3:
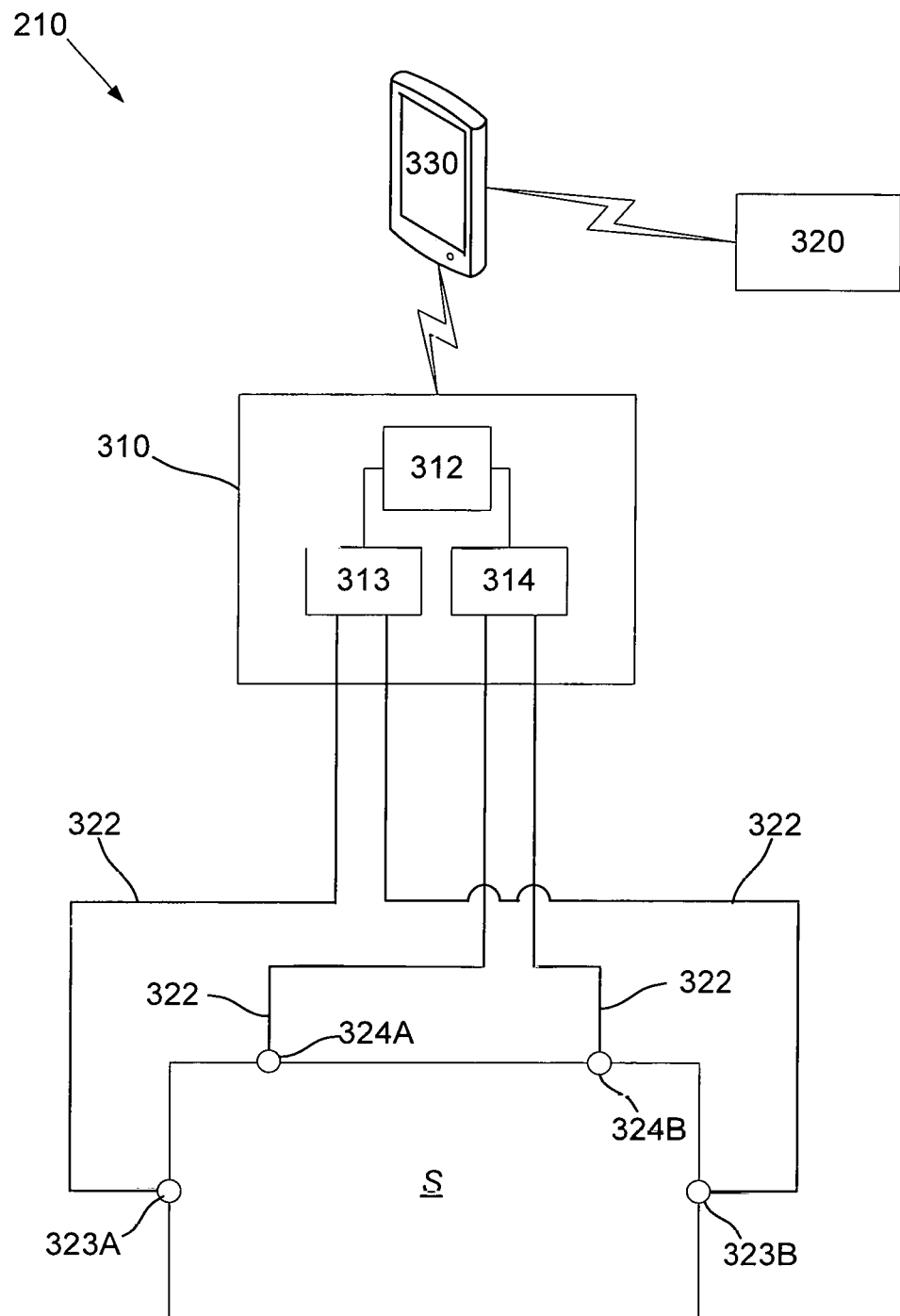
FIG. 3 is a schematic diagram of a measuring system.

An example measuring system will now be described in further detail with reference to FIG. 3.

In this example, the measuring system includes an impedance measuring unit having an impedance measuring device 310, which is in turn in communication with a processing system in the form of a client device 330, such as a portable computer system, mobile phone, tablet or the like. One or more optional sensors can be provided for capturing other relevant information. These could include physical characteristic sensors 320, which can also be provided for capturing information regarding physical characteristics of an individual/subject.

The nature of the physical characteristic sensors 320 will vary depending on the characteristics to be measured, and could include for example scales for measuring an individual/subject's weight and/or an image capture device, such as a camera, body scanner, DEXA (Dual-Energy X-ray Absorptiometry), 3D laser or optical scanning, or the like, for measuring a height and/or body segment dimensions, as will be described in more detail below. Additionally or alternatively, this could include electronic scales for measuring a weight, and other monitoring equipment, for example for measuring heart rate, blood pressure or other characteristics.

However, additional sensors could also include sensors for detecting other relevant information. For example, this could include sensors for detecting environmental characteristics, such as a temperature and/or humidity, location sensors for tracking a location, or fitness sensors for sensing fitness data, such as a number of steps taken, distance traversed, or the like. The sensors can be part of separate sensing devices, or could form part of the client device 330.

The impedance measuring device 310 typically includes a measuring device processor 312 coupled to at least one signal generator 313 and at least one sensor 314, which are in turn coupled to respective drive and sense electrodes 323A, 323B and 324A, 324B, via leads 322. In use, the signal generator 313 generates a drive signal, which is applied to the individual/subject S via the drive electrodes 323A, 323B, whilst the sensor 314 measures a response signal via the sense electrodes 324A, 324B. In use, the measuring device processor 312 controls the at least one signal generator 313 and the at least one sensor 314, allowing the impedance measurements to be performed.

In particular, the measuring device processor 312 is adapted to generate control signals, which cause the signal generator 313 to generate one or more alternating signals, such as voltage or current signals of an appropriate waveform, which can be applied to a subject S, via the first electrodes 323A, 323B and processing received signals from the sensor 314. It will be appreciated that the measuring device processor 312 may be any form of electronic processing device capable of performing appropriate control, and could include an FPGA (field programmable gate array), or a combination of a programmed computer system and specialised hardware, or the like.

The signal generator 313 could be of any appropriate form, but will typically include digital to analogue converters (DACs) for converting digital signals from the processing device to analogue signals, which are amplified to generate the required drive signals, whilst the sensor 314 typically includes one or more amplifiers for amplifying sensed response signals and analogue to digital converters (ADCs) to digitise the analogue response signals and providing digitised response signals to the processing device.

The nature of the alternating drive signal will vary depending on the nature of the measuring device and the subsequent analysis being performed. For example, the system can use Bioimpedance Analysis (BIA) in which a single low frequency signal is injected into the subject S, with the measured impedance being used directly in the determination of biological parameters. In one example, the applied signal has a relatively low frequency, such as below 100 kHz, more typically below 50 kHz and more preferably below 10 kHz. In this instance, such low frequency signals can be used as an estimate of the impedance at zero applied frequency, commonly referred to as the impedance parameter value $R_0$, which is in turn indicative of extracellular fluid levels.

Alternatively, the applied signal can have a relatively high frequency, such as above 200 kHz, and more typically above 500 kHz, or 1,000 kHz. In this instance, such high frequency signals can be used as an estimate of the impedance at infinite applied frequency, commonly referred to as the impedance parameter value Rte, which is in turn indicative of a combination of the extracellular and intracellular fluid levels, as will be described in more detail below.

Alternatively and/or additionally, the system can use Bioimpedance Spectroscopy (BIS) in which impedance measurements are performed at each of a number of frequencies ranging from very low frequencies (1 kHz and more typically 3 kHz) to higher frequencies (1,000 kHz), and can use as many as 256 or more different frequencies within this range. Such measurements can be performed by applying a signal which is a superposition of plurality of frequencies simultaneously, or a number of alternating signals at different frequencies sequentially, depending on the preferred implementation. The frequency or frequency range of the applied signals may also depend on the analysis being performed.

When impedance measurements are made at multiple frequencies, these can be used to derive one or more impedance parameter values, such as values of $R_0$, $Z_c$, $R_\infty$, which correspond to the impedance at zero, characteristic and infinite frequencies. These can in turn be used to determine information regarding both intracellular and extracellular fluid levels, as will be described in more detail below.

A further alternative is for the system to use Multiple Frequency Bioimpedance Analysis (MFBIA) in which multiple signals, each having a respective frequency are injected into the subject S, with the measured impedances being used in the assessment of fluid levels. In one example, four frequencies can be used, with the resulting impedance measurements at each frequency being used to derive impedance parameter values, for example by fitting the measured impedance values to a Cole model, as will be described in more detail below. Alternatively, the impedance measurements at each frequency may be used individually or in combination.

Thus, the measuring device 310 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied. In one example, the voltage source is typically symmetrically arranged, with two signal generators 313 being independently controllable, to allow the signal voltage across the subject to be varied, for example to minimise a common mode signal and hence substantially eliminate any imbalance as described in copending patent application number WO2009059351.

As the drive signals are applied to the subject, the sensor 314 then determines the response signal in the form of the voltage across or current through the subject S, using second electrodes 324A, 324B. Thus, a voltage difference and/or current is measured between the second electrodes 324. In one example, a voltage is measured differentially, meaning that two sensors 314 are used, with each sensor 314 being used to measure the voltage at each second electrode 324 and therefore need only measure half of the voltage as compared to a single ended system. Digitised response signals are then provided to the measuring device processor 312, which determines an indication of the applied drive signal and measured response signals, and optionally uses this information to determine measured impedances.

Thus, in the above arrangement, four electrodes are shown, with two forming drive electrodes and two forming sense electrodes. However, this is not essential, and any suitable number of electrodes could be used. Furthermore, a single signal generator and sensor are shown, but again a respective signal generator and sensor could be used for each drive and sense electrode, respectively, and the described arrangement is for the purpose of illustration only.

In the above arrangement, the client device 330 is coupled to the measuring device processor 312, allowing operation of the impedance measuring device to be controlled. In particular, the client device 330 can be used to instruct the measuring device processor 312 on a particular sequence of impedance measurements that need to be performed, further receiving either an indication of the drive/sense signals and/or measured impedance values. The client device 330 can then optionally perform further processing, for example to determine the impedance indicators, although alternatively this may not be required and raw impedance data could be provided to the server 250 for analysis.

The client device 330 can also combine impedance values or indicators with information regarding indications of body states and physical characteristics determined either by manual user input or based on signals from one or more physical characteristic sensors. This allows the client device to generate the reference data, which is then transferred via the communications network 240 to the server 250. However, alternatively, the server 250 could obtain the indication of body states and/or physical characteristic from other data sources, depending on the preferred implementation.

Figure 4:
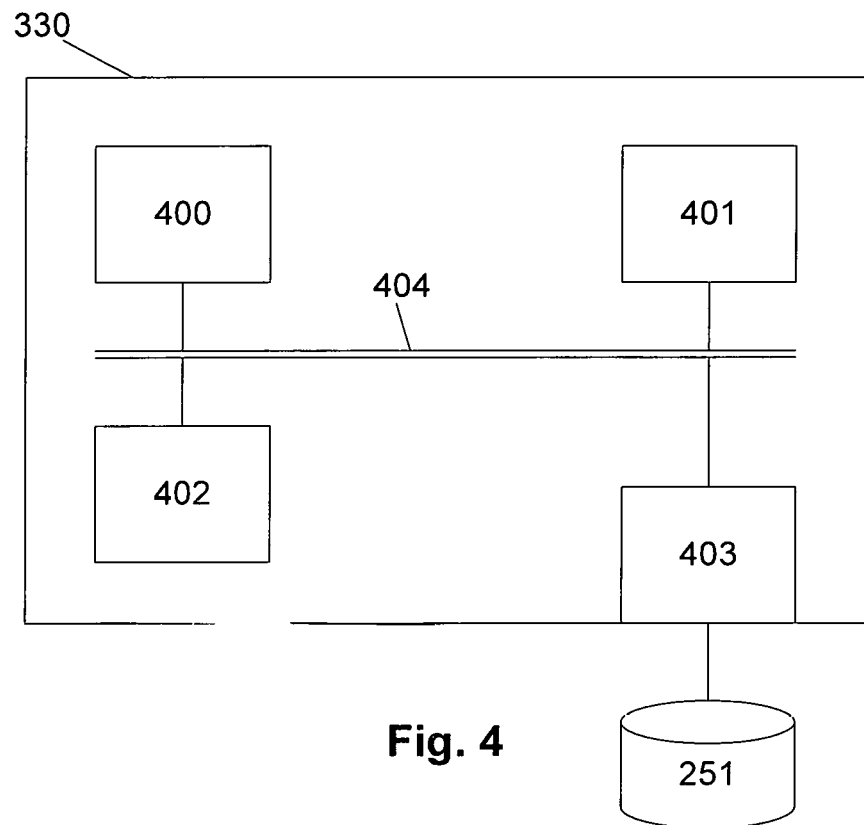
FIG. 4 is a schematic diagram of an example of a client device.

Accordingly, it will be appreciated that the client device 330 can be of any appropriate form and one example is shown in FIG. 4. In this example, the client device 330 includes at least one microprocessor 400, a memory 401, an input/output device 402, such as a keyboard and/or display, and an external interface 403, interconnected via a bus 404 as shown. The external interface 403 can be utilised for connecting the client device 330 to peripheral devices, such as the communications networks 240, databases, other storage devices, or the like. Although a single external interface 403 is shown, this is for the purpose of example only, and in practice multiple interfaces using various methods (e.g. Ethernet, serial, USB, wireless or the like) may be provided.

In use, the microprocessor 400 executes instructions in the form of applications software stored in the memory 401 to allow communication with the server 250, for example to allow reference data to be provided to the sever, or the like.

Accordingly, it will be appreciated that the client device 330 may be formed from any suitable processing system, such as a suitably programmed PC, Internet terminal, laptop, or hand-held PC, and in one preferred example is either a tablet, or smart phone, or the like. Thus, in one example, the client device 330 is a standard processing system such as an Intel Architecture based processing system, which executes software applications stored on non-volatile (e.g., hard disk) storage, although this is not essential. However, it will also be understood that the client devices 330 can be any electronic processing device such as a microprocessor, microchip processor, logic gate configuration, firmware optionally associated with implementing logic such as an FPGA (Field Programmable Gate Array), or any other electronic device, system or arrangement.

Figure 5:
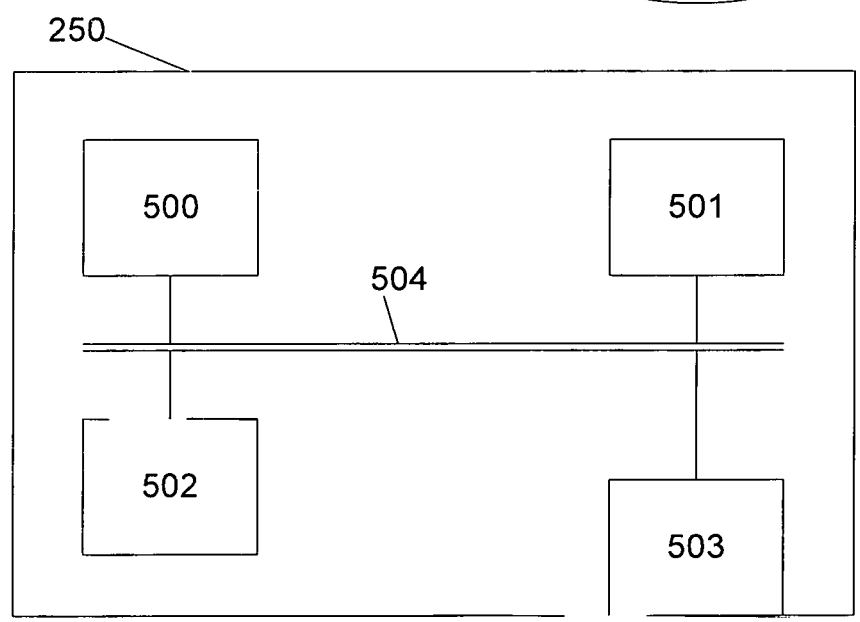
FIG. 5 is a schematic diagram of an example of a server.

An example of a suitable server 250 is shown in FIG. 5. In this example, the server includes at least one microprocessor 500, a memory 501, an optional input/output device 502, such as a keyboard and/or display, and an external interface 503, interconnected via a bus 504 as shown. In this example the external interface 503 can be utilised for connecting the server 250 to peripheral devices, such as the communications networks 240, databases 251, other storage devices, or the like. Although a single external interface 503 is shown, this is for the purpose of example only, and in practice multiple interfaces using various methods (eg. Ethernet, serial, USB, wireless or the like) may be provided.

In use, the microprocessor 500 executes instructions in the form of applications software stored in the memory 501 to allow the required processes to be performed, including communicating with the client devices 330, and optionally receiving, analysing and/or displaying results of impedance measurements. The applications software may include one or more software modules, and may be executed in a suitable execution environment, such as an operating system environment, or the like.

Accordingly, it will be appreciated that the server 250 may be formed from any suitable processing system, such as a suitably programmed client device, PC, web server, network server, or the like. In one particular example, the server 250 is a standard processing system such as an Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement. Accordingly, whilst the term server is used, this is for the purpose of example only and is not intended to be limiting.

Whilst the server 250 is a shown as a single entity, it will be appreciated that the server 250 can be distributed over a number of geographically separate locations, for example by using processing systems and/or databases 251 that are provided as part of a cloud based environment. For example, different servers might be provided that perform different functionality, such as analysing data to generate reference signatures, analysing subject signatures, hosting medical records, or the like. Thus, the above described arrangement is not essential and other suitable configurations could be used.

Figure 6A:
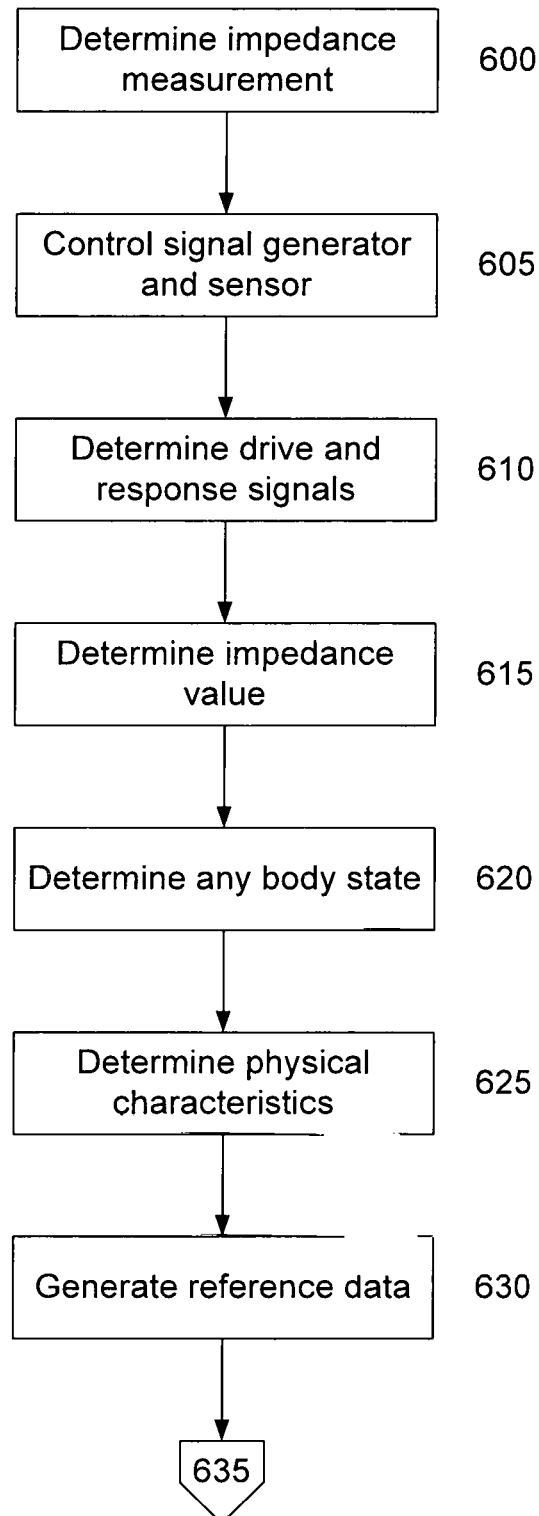
FIGS. 6A to 6C are a flowchart of a further example of a method for determining reference signatures and using the reference signatures to assist identification of a body state of a subject.
Figure 6B:
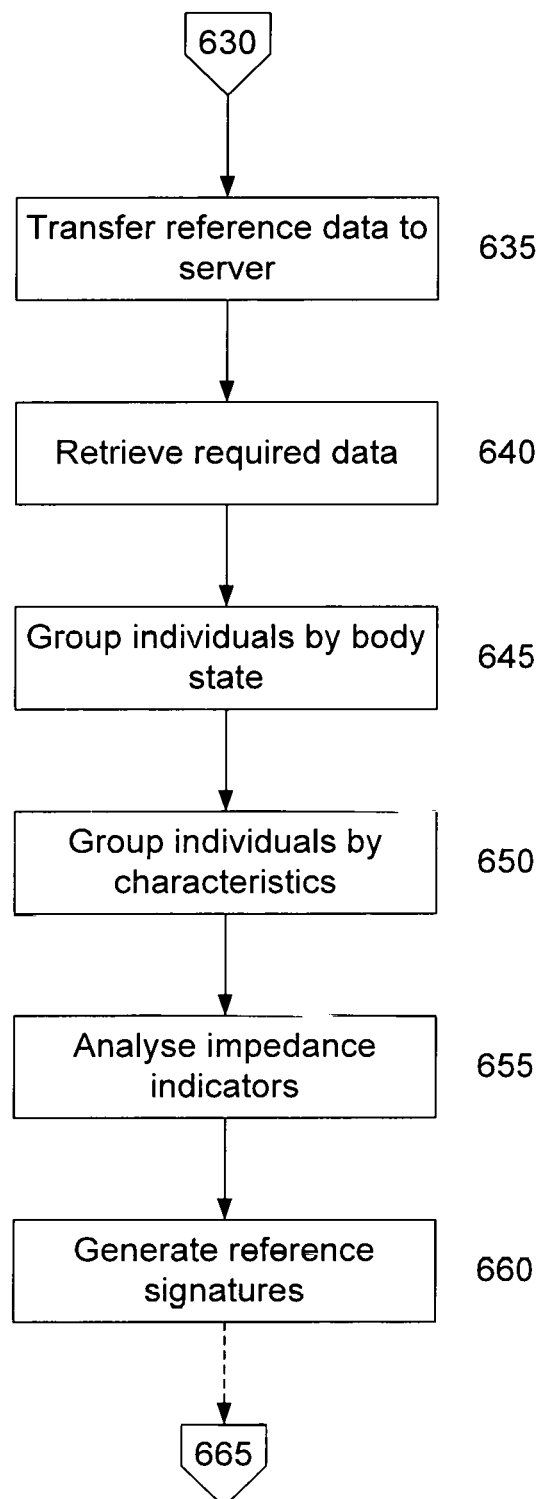
Figure 6C:
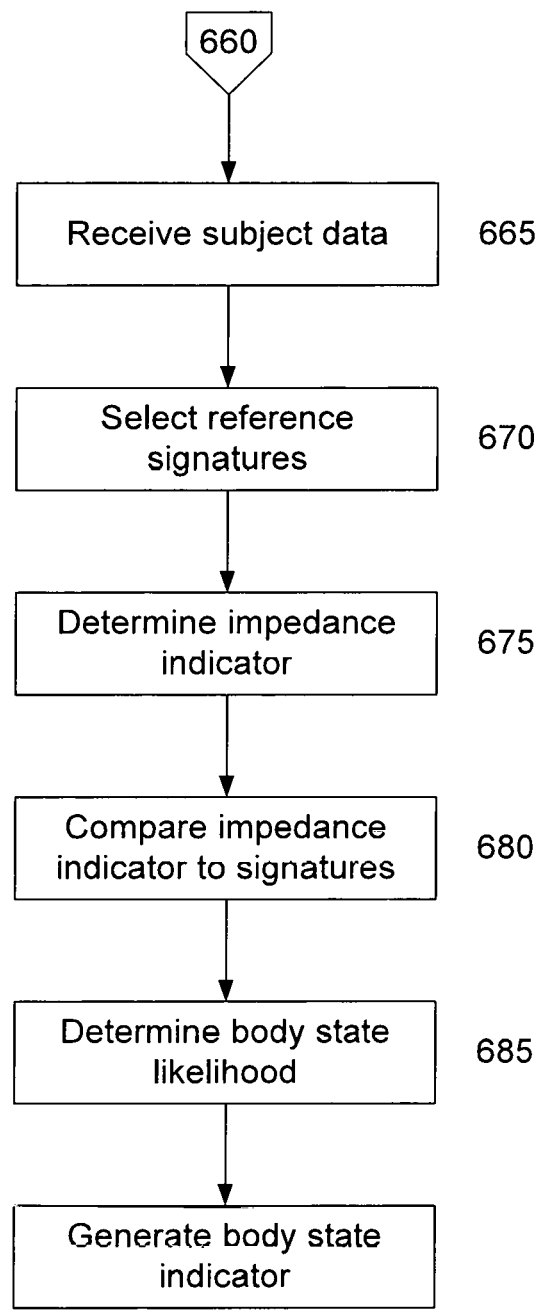

Operation of the system will now be described in further detail with reference to FIGS. 6A to 6C.

For the purpose of these examples it will also be assumed that users use the client devices 330 to control the measuring device 310 and any characteristic or other sensors, allowing impedance or other measurements to be performed and allowing information regarding physical characteristics or other sensed attributes to be collected. This is typically achieved by having the user interact with the system via a GUI (Graphical User Interface), or the like presented on the client device 330, which may be generated by a local application, or hosted by the server 250, which is typically part of a cloud based environment, and displayed via a suitable application, such as a browser or the like, executed by the client device 330. Actions performed by the client device 330 are typically performed by the processor 400 in accordance with instructions stored as applications software in the memory 401 and/or input commands received from a user via the I/O device 402. Similarly, actions performed by the server 250 are performed by the processor 500 in accordance with instructions stored as applications software in the memory 501 and/or input commands received from a user via the I/O device 502, or commands received from the client device 330.

The system utilises multiple measuring and client devices 310, 330, which interact with one or more central servers 250, typically forming part of a cloud based environment.

This allows reference and subject data to be collected from a number of different sources, and then aggregated and analysed centrally.

Whilst the following example focuses on the analysis of impedance indicators only, it will be appreciated that the techniques could be extended to include other body parameters as part of the reference signature, and reference to impedance indicators only is not intended to be limiting.

However, it will be appreciated that the above described configuration assumed for the purpose of the following examples is not essential, and numerous other configurations may be used. It will also be appreciated that the partitioning of functionality between the measuring device 310, client devices 330, and servers 250 may vary, depending on the particular implementation.

At step 600, the measuring device processor 312 determines the impedance measurement to be performed. This can be achieved in any suitable manner, but would typically include having the user selecting one of a number of available measuring procedures presented on the client device 330, with the client device 330 generating instructions which are provided to the measuring device processor 312.

Prior to a measurement being performed, the first and second electrodes 323, 324 are positioned on the subject to allow one or more signals to be injected into the subject S, and allowing a response signal to be measured. The location of the electrodes 323, 324 will depend on the segment of the subject S under study. Thus, for example, the electrodes 323, 324 can be placed on the thoracic and neck region of the subject S to allow the impedance of the chest cavity to be determined. Alternatively, positioning electrodes on the wrist and ankles of a subject, or in contact with the hands and feet, allows the impedance of limbs, torso and/or the entire body to be determined.

At step 605, the measuring device processor 312 controls the signal generator and sensor, causing the drive signals to be applied to the individual/subject and causing the corresponding response signals to be measured, allowing the measuring device processor 312 to determine both the drive and response signals at step 610.

In this regard, the response signal will be a superposition of voltages generated by the human body, such as the ECG (electrocardiogram), voltages generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise.

Other suitable digital and analogue demodulation techniques will be known to persons skilled in the field.

At step 615, the drive and response signals are used to determine an impedance indicator, such as an impedance value, or impedance parameter value. This can be performed by the measuring device 310 alone, but more typically is performed in conjunction with the client device 330, with the measuring device providing an indication of measured impedance values to the client device 330, which then analyses these to determine the impedance indicators.

For example, in the case of BIS, impedance or admittance measurements are determined from the signals at each frequency by comparing the recorded voltage and the current through the subject. The demodulation algorithm can then produce amplitude and phase signals at each frequency, allowing an impedance value at each frequency to be determined.

Whilst the measured impedance can be used directly, in one example, the measured impedance is used to derive an impedance parameter, and in particular an impedance (resistance) at zero frequency, $R_0$, equals the extracellular resistance $R_e$.

Figure 7A:
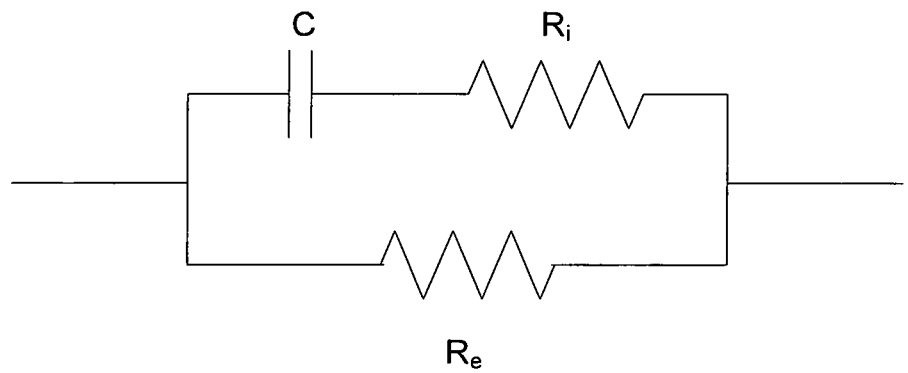
FIG. 7A is schematic diagram of an example of a theoretical equivalent circuit for biological tissue.

In this regard, FIG. 7A is an example of an equivalent circuit that effectively models the electrical behaviour of biological tissue. The equivalent circuit has two branches that represent current flow through extracellular fluid and intracellular fluid, respectively. The extracellular fluid component of biological impedance is represented by an extracellular resistance $R_e$, whilst the intracellular fluid component is represented by an intracellular resistance $R_i$ and a capacitance C representative of the cell membranes.

The relative magnitudes of the extracellular and intracellular components of impedance of an alternating current (AC) are frequency dependent. At zero frequency the capacitor acts as a perfect insulator and all current flows through the extracellular fluid, hence the resistance at zero frequency, $R_0$, equals the extracellular resistance $R_e$. At infinite frequency the capacitor acts as a perfect conductor and the current passes through the parallel resistive combination. The resistance at infinite frequency is given by:

$$R_\infty = \frac{R_e R_i}{R_e + R_i} \quad (1)$$

Hence the intracellular resistance is given by:

$$R_i = \frac{R_\infty R_e}{R_e + R_\infty} \quad (2)$$

Accordingly, the impedance of the equivalent circuit of FIG. 3A at an angular frequency $\omega$, where $\omega = 2\pi*$frequency, is given by:

$$Z = R_\infty + \frac{R_0 - R_\infty}{1 + (j\omega\tau)} \quad (3)$$

where: $R_x$=impedance at infinite applied frequency
$R_0$=impedance at zero applied frequency=$R_e$ and,
$\tau$ is the time constant of the capacitive circuit.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^\alpha} \quad (4)$$

where: α has a value between 0 and 1 and can be thought of as an indicator of the deviation of a real system from the ideal model.

Figure 7B:
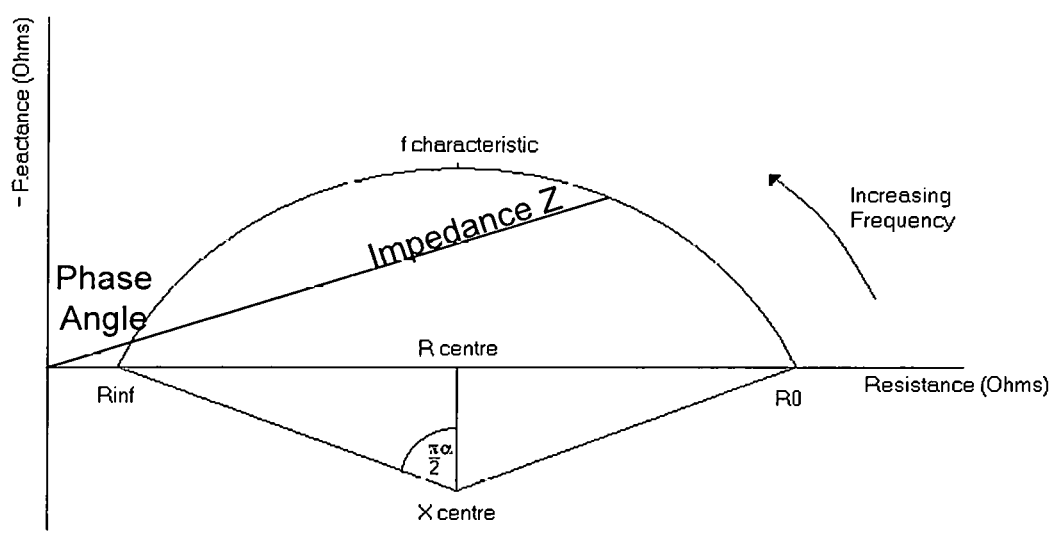
FIG. 7B is an example of a locus of impedance known as a Wessel-plot.

An example of the typical multi-frequency impedance response is shown in FIG. 7B. As frequency increases, the reactance increases to a peak at the characteristic frequency and then decreases while the resistance continually decreases. This results in a circular locus with the centre of the circle below the x axis, as shown.

The values of impedance parameters $X_c$, $R_0$, $R_\infty$, $Z_c$ or α may be determined in any one of a number of manners such as by:
  estimating values based on impedance measurements performed at selected respective frequencies;
  solving simultaneous equations based on the impedance values determined at different frequencies;
  using iterative mathematical techniques;
  extrapolation from a plot of resistance against reactance for impedance measurements at a plurality of frequencies (a "Wessel plot" similar to that shown in FIG. 3B);
  performing a function fitting technique, such as the use of a polynomial function.

For example, the Wessel plot is often used in BIS devices, which perform multiple measurements over a range of frequencies, such as from 1 kHz to 1,000 kHz, using 256 or more different frequencies within this range. A regression procedure is then used to fit the measured data to the theoretical semi-circular locus, allowing values for $X_c$, $R_0$, $R_\infty$, $Z_c$ or α to be calculated. Alternatively, a circle fitting technique can be used in which three simultaneous equations representing the geometric relationships between points on a circle are solved to allow calculation of the radius (r) and the co-ordinates of the centre of the circle (i, j) as the three parameters which define the circle.

In one example, the frequencies used are in the range 0 kHz to 1,000 kHz, and in one specific example, four measurements are recorded at frequencies of 25 kHz, 50 kHz, 100 kHz, and 200 kHz, although any suitable measurement frequencies can be used.

A further alternative for determining impedance parameter values such as $X_c$, $R_0$, $R_\infty$, $Z_c$ or α is to perform impedance measurements at a single frequency, and use these as an estimate of the parameter values. In this instance, measurements performed at a single low frequency (typically less than 50 kHz) can be used to estimate $R_0$, measurements at a single high frequency (typically more than 100 kHz) can be used to estimate $R_\infty$, allowing a value of $R_i$ to be determined using equation (2) above.

The above described equivalent circuit models the resistivity as a constant value and does not therefore accurately reflect the impedance response of a subject, and in particular does not accurately model the change in orientation of the erythrocytes in the subject's blood stream, or other relaxation effects. To more successfully model the electrical conductivity of the human body, an improved CPE based model may alternatively be used.

In any event, it will be appreciated that any suitable technique for determination of the parameter values such as $R_0$, $Z_c$, $R_\infty$, and $X_c$ may be used, hence allowing R to be derived.

It will also be appreciated that the apparatus could be used to determine other body parameters. In one example, this can be achieved by using the apparatus passively to record body signals using the sense electrodes and sensors 324, 314 to monitor voltage signals within the body, such as ECG signals. The detected signals are a superposition of voltages generated by the human body, and will include cardiac and respiratory components, which can typically be isolated through suitable filtering, for example 1-40 Hz for cardiac signals and below 1 Hz for respiratory signals.

In any event, at step 620, the client device 330 determines one or more body states, such as disease and/or wellness states. This can be performed by having the client device display a suitable user interface, allowing a user, such as a medical practitioner, to enter the information manually, for example by selecting from a drop down list, categories or the like. Alternatively, the user could use the client device 330 to retrieve the information from a database, such as an electronic medical record or the like, or alternatively provide information allowing an indication of the body states to be retrieved by the server 250, for example by providing an identifier associated with the individual, allowing the server 250 to retrieve the individual's medical records.

At step 625, the client device 330 determines physical characteristics of the individual. Again, this could be achieved by manual input via a user interface and/or by receiving data from the sensing device 320, as will be described in more detail below. At this time, additional data can be collected, such as environmental characteristics, allowing this to be used to further stratify the reference signatures.

At step 630, the client device 330 generates the reference data, which is then transferred to the server 250 at step 635 for analysis. The reference data can be indicative of, or include measured raw signal and/or indicators or body parameter values derived therefrom, including but not limited to impedance values, impedance parameter values, vital signs indicators, a cardiac parameter value, a respiratory parameter value, a blood potassium level, a fitness parameter, a temperature, a blood pressure, a respiratory rate, a heart rate or the like. This will also include details of any other characteristics measured, including environmental characteristics, such as a temperature, location, humidity or the like.

At step 640, the server 250 retrieves any required information. For example, if information regarding a body state and/or physical or other characteristics have not been provided, and this is available from another source, such as medical records or the like, this information can be retrieved before analysis of the reference data is performed in order to generate reference signatures for each of a plurality of different body states.

In order to achieve this, at step 645, the server 250 allocates each individual to a respective group based on any body states identified for the individual. Thus, a group of individuals is formed for each of a plurality of different body states. At step 650, each group is further divided into sub-groups based on physical characteristics of the individuals and optionally for each of a plurality of environmental characteristics relevant to the individual. In particular, the server examines the physical characteristics for each individual and then allocates the individual to a respective sub-group so that each individual within the sub-group has respective physical characteristics in common. Similarly, the server can examine the environmental characteristics, and allocate the individual to a respective sub-group of individuals having environmental characteristics in common.

It will be appreciated that the manner in which this division occurs can vary depending on a number of factors, including the preferred implementation, the particular physical characteristics, the body state or the like. For example, individuals could be allocated to different groups based on one or more of the individual's sex, ethnicity, age, weight or height. Thus, for example, a number of sub-groups could be defined for particular ranges of age, weight and height, with the individual being allocated to the group as appropriate according to their physical and/or environmental characteristics.

Additionally, it is possible for multiple different overlapping sub-groups to be created for different combinations. For example, a respective group could be formed for all male and all female individuals, with separate additional groups being formed for male/female individuals of particular age ranges, meaning that individuals can be allocated to multiple sub-groups.

It will also be appreciated that the groups formed may differ depending on the respective body state. For example, a low prevalence of some body states in young people may mean that groups for that body state will span a larger age range than for other body states. Similarly, when taking into account environmental characteristics, such as the individual's location, groups could be established which are national, with separate groups being established which are local, such as town and/or city based.

At step 655, the server 250 analyses the impedance indicators, and optionally other body parameters, for each group to generate the reference signatures. In one example, this involves determining a distribution of impedance indicators for each group. This can involve simply using measured impedance values, or alternatively could involve analysing impedance values to determine impedance parameter values, such as $R_0$, $R_x$, or the like, or could involve determining fluid level indicators, for example indicative of levels of extracellular fluid, intracellular fluid, or a ratio of the two.

It will also be appreciated that different impedance indicators could be used for different body states, depending on the indicator that is most effective at identifying the presence, absence, degree or severity of the respective body states. For example, the reference signature for heart failure may be based solely on an extracellular fluid level indicator, which is sufficiently capable of identifying if an individual has heart failure, whereas other body states may require an extracellular to intracellular fluid level ratio. Similarly, mere identification of the presence or absence of a disease may be achieved using a basic impedance indicator, whereas distinguishing the severity of the disease may require more complex indicators.

Additionally multiple different indicators can be used in parallel in a multi-dimensional approach, for example examining multiple different impedance indicators for multiple different body segments, both individual and relatively, such as examining relative values of intracellular and extracellular fluids for different body segments, such as limbs and the torso.

At step 660, the server 250 uses the analysed impedance indicators, and in particular the distribution(s) to form a respective reference signature for each group. The reference signature could be a simple threshold range of extreme indicator values (typically upper and lower end) associated with a particular group, allowing direct comparison to the range. Alternatively, the reference signature is representative of a range of values and frequency of occurrence of each value. For example, this can involve performing a statistical analysis to extrapolate a likely distribution curve based on the relative frequency of impedance indicators of the individuals within the respective group, optionally taking into account exclusion of outlier values or the like. The signature could be expressed in any form, and could be a simple range or multi-dimensional vector including dimensions corresponding to each of a number of different impedance indicators.

Accordingly, it will be appreciated that the above described process leads to the generation of reference signatures that can then be used in the identification of a range of different body states. It will also be appreciated that as additional reference data is collected, the reference signatures can be continuously or periodically updated, meaning the reference signatures will be refined as additional reference data is collected.

Once generated, the reference signatures can be used to generate a body state indicator for use in diagnosing a subject with one or more body states and an example of this will now be described.

At step 665, subject data is collected and provided to the server 250. The subject data typically includes impedance values and/or impedance indicators measured for the subject, as well as details of the subject's physical characteristics or environmental characteristics. Accordingly, it will be appreciated that the subject data can be collected by a measuring system using the client device 330 in a similar manner to that described above with respect to collection of the reference data in steps 600 to 630, albeit optionally without any indication of a body state. Collection of subject data will not therefore be described in further detail. It will also be appreciated that as part of this step, any required data which is not collected by measurement could be retrieved from a suitable source, such as a medical record of the subject.

At step 670, the server 250 selects reference signatures for each of a plurality of body states based on the physical characteristics of the subject and/or the environmental characteristics associated with the user. Thus, the server 250 will identify reference signatures corresponding to the sub-groups of individuals having physical characteristics and/or environmental characteristics in common with the subject. The server 250 will then determine or calculate subject impedance indicators from the received subject data, based on the type of impedance indicator required for each reference signature at step 675. A similar approach could also be used for other body parameters, such as other vital signs indicator or the like.

At step 680, the server 250 compares the impedance indicators to the respective reference signatures to determine a likelihood of the subject having one or more respective body states at step 685. An example of this will now be illustrated with reference to FIG. 8.

Figure 8:
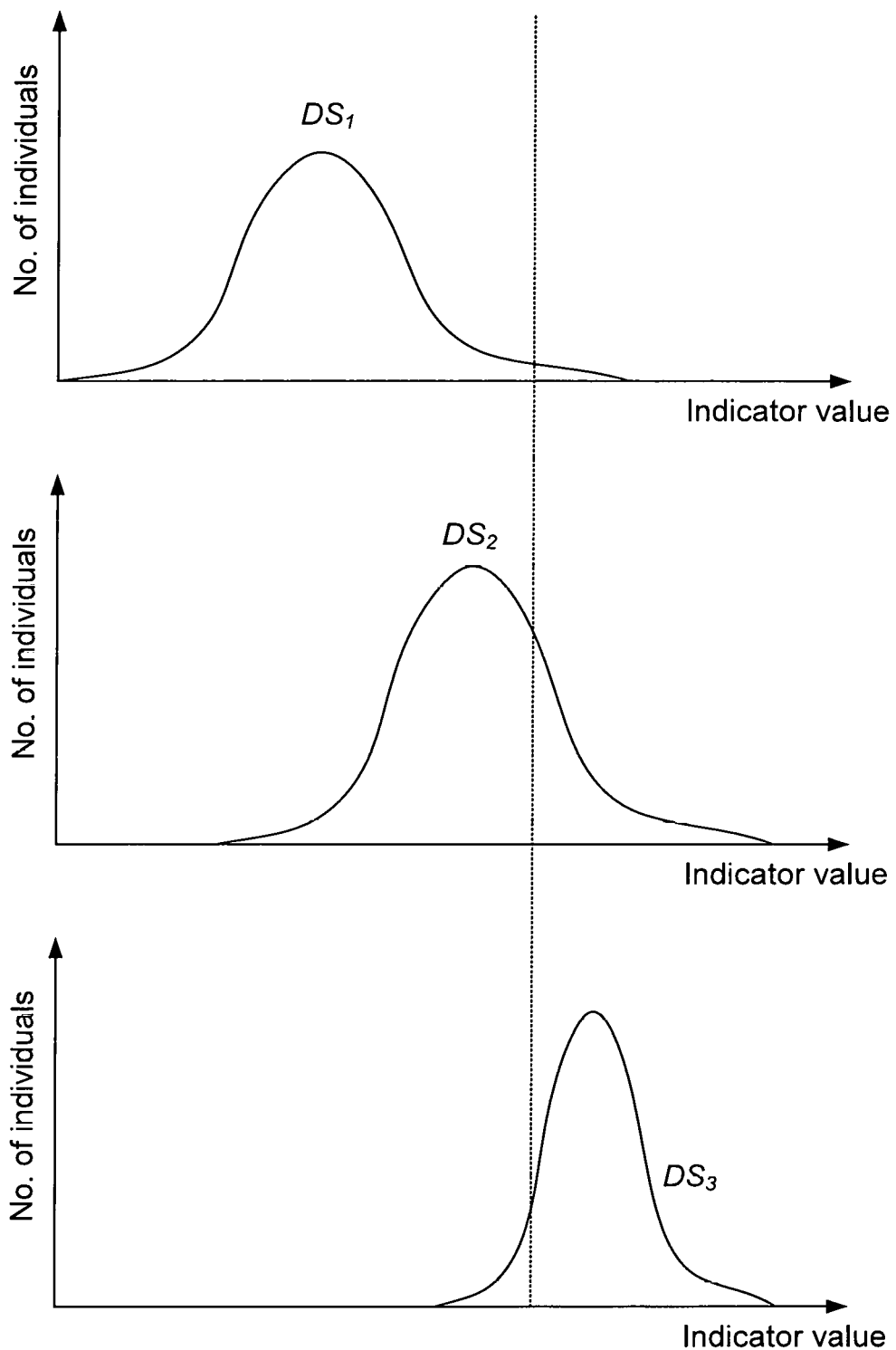
FIG. 8 is a schematic diagram illustrating example reference signatures.

In this regard, FIG. 8 shows reference signatures for three respective body states, identified as $DS_1$, $DS_2$, $DS_3$. In this regard, the body states could correspond to different diseases and/or a healthy state. Additionally or alternatively these different states could correspond to respective severities of a single body state, for example indicating whether a single disease is mild, moderate or severe. In any event, it can be seen that the distributions representing the respective reference signatures overlap. Accordingly, for an impedance indicator represented by the dulled line, this suggests the likelihood of the subject having the respective body states is minimal for $DS_1$, high for $DS_2$, and low for $DS_3$.

It will be appreciated that the above described example is a simplistic example based on a single indicator value and that in practice a multi-dimensional approach would be used including a reference signature including one or more reference impedance indicator values/ranges and optionally one or more other body parameter or vital sign indicator values/ranges would be used. In this example, the signatures could be expressed as vectors, with a subject vector being compared to the reference signature vectors by performing a proximity assessment in a multi-dimensional vector space, with a likelihood of a body state being based on the relative proximity of the subject vector to the reference signature vectors. It will be appreciated that a likelihood could be calculated for multiple different body state, based on a relative similarity of the subject signature to multiple reference signatures.

Once the comparison has been performed and likelihood(s) of any body states determined, an indication of this can be generated at step 690 and then provided either to the subject, or more likely a medical practitioner, for example by providing this to the client device 330 of one of the measuring systems 210.

In this regard, the body state indicator could be of any appropriate form and could include for example, a percentage likelihood or body state score indicative of the likelihood of the subject having each of one or more body states. Thus, this could be a numeric value scaled between 1 and 10, with 1 indicative of a low likelihood and 10 a high likelihood or vice versa. Additionally, or alternatively this could be presented as a graphical representation, for example using a pointer and scale to indicate the likelihood of the subject having a condition, or could include information regarding results of the comparison, for example showing graphs similar to those shown in FIG. 8, allowing a medical practitioner to understand the outcome of the analysis and how any indicator has been determined, which can facilitate a identification process.

Accordingly, it will be appreciated that the above described process can assist medical personnel in performing a identification and/or treating a subject.

As previously discussed, the collection of reference data can be performed during a body composition measurement process, which may in turn utilise physical characteristic information, and in particular information regarding dimensions of an individual or segments of an individual. This is particularly advantageous as it means that physical characteristics required in order to segment the reference individuals into groups and hence generate accurate reference signatures, will automatically be collected as part of the impedance measurement and analysis process.

Figure 9:
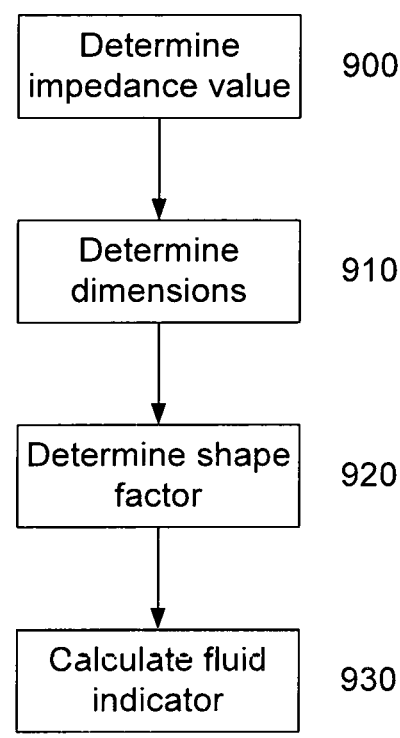
FIG. 9 is a flowchart of an example of a process for use in determining fluid levels within a subject.

An example process for performing body composition measurements will now be described with reference to FIG. 9. For the purpose of this example, it is assumed that impedance measurements are being performed using the measuring system 210 described above. For the purpose of ease of explanation, this example will focus on the collection of subject data from a subject, but it will be appreciated that the techniques would also apply to collection of reference data and the terms individual and subject should be considered as interchangeable throughout the following.

In this example, at step 900, measured voltage and current signals are used by either the measuring device processor 312 or the client device 330 to determine at least one impedance value at at least one frequency, the at least one impedance value representing an impedance measured for the subject. The impedance could be of one or more segments of the subject and/or of the whole body, depending on the preferred implementation, and as will be described in more detail below. Whilst the measured impedance can be used directly, in one example, the measured impedance is used to derive an impedance parameter value, as previously described.

At step 910 physical dimensions for at least part of at least one segment of the subject are determined. The manner in which this is achieved will vary depending on the preferred implementation and could include physically measuring the dimensions of the segments of the subject, and then inputting this information into the client device 330. However, this suffers from a number of drawbacks, including being arduous, time consuming and requiring manual entry of data, which is subject to error. Alternatively, the dimensions could be derived from other more easily measured physical characteristics, such as the height, weight, sex and age of a subject. More preferably however, the dimensions could be determined using a characteristic sensor 320 capable of detecting the physical characteristics. This could include for example an imaging system capable of performing 2D or 3D imaging of an individual/subject, for example using a camera and/or laser scanner, to image the based on dimensions measured from images of a subject, as will be described in more detail below.

At step 920, the client device 330 uses the dimensions to calculate a shape factor. The shape factor is used to scale the impedance measurements in order to take into account the shape of the segments of a subject, before a fluid indicator indicative of the levels of extracellular fluid is calculated at step 930.

In this regard, in the Hanai approach to body composition estimation initial estimates of body volume and shape are very important. For a uniform conductor, such as a cylinder, resistance R is related to length H and volume V by the well-known relationship:

$$V = \frac{\rho H^2}{R} \quad (5)$$

where: ρ is the resistivity of the conductor material

For a body of a different shape, a scale-independent shape factor can be used to correct the relationship:

$$V = K\frac{\rho H^2}{R} \quad (6)$$

where: K is shape factor

In the specific example of human whole body measurements, the shape factor $K_B$ accounts for the facts that the human body is not a simple cylinder and that the measurement region sampled by the electrical signal includes one arm, one leg and the trunk, but the remaining limbs and head are additional unmeasured mass. However, this is equally applicable to segmental analysis in which the shape factor $K_S$ represents deviation in volume of the segment from a cylindrical shape.

When determining extracellular fluid levels from a measurement of the impedance, the impedance used is often that of the impedance at zero applied frequency $R_0$, or an impedance value measured at a single low frequency, such as 30 kHz, as an estimate of $R_0$, in which case the resistivity in equation (6) will not be the actual resistivity of the extracellular fluid, but an apparent higher resistivity value. This is because the extracellular fluid contains a large number of non-conductive elements (cells) distributed through it. Cell walls are non-conductive at low frequencies.

The apparent resistivity is given by a special case of Hanai's theory where a conductive medium contains a dispersion of particles whose resistivity is very much higher than that of the conductive medium itself.

$$\rho_{apparent} = \frac{\rho_{ecf}}{(1-c)^{3/2}} \quad (7)$$

where: c is the volume concentration of the non-conductive elements in the conductive medium.

The apparent resistivity will therefore depend on the relative concentrations of extracellular fluid and cellular material containing intracellular fluid. These are values which are not expected to be constant, so an expression which uses the true ECF resistivity is needed.

Combining equations (7) with (6) and rearranging, the expression for the extracellular fluid volume $V_{ecf}$ becomes:

$$V_{ecf} = \left(K \frac{\rho_{ecf} H^2}{R_0}\right)^{2/3} \cdot V_{WB}^{1/3} \quad (8)$$

where: $V_{WB}$ is the total body volume,
$\beta_{ecf}$ is the true resistivity of ECF
For fluid levels in general, a similar equation could be used as follows:

$$V = \left(K \frac{\rho H^2}{R}\right)^{2/3} \cdot V_{WB}^{1/3} \quad (9)$$

where: V is the fluid volume
ρ is the true resistivity of the fluid
R is the impedance Usually body volume is approximated by using the subject's weight divided by a body density constant (1.05). Equation (8) is written here in a slightly different form to that generally published to make clearer how it is a development of (6).

It should be noted however that this results in assumptions regarding the fact that the extracellular fluid contains a dispersion of cells which are non-conductive at low frequencies. The extracellular fluid term and the whole body term are weighted by the powers of ⅔ and ⅓ respectively. If the distribution of non-conductive elements becomes less disperse, the values of the powers will change, so a more general equation would be:

$$V_{ecf} = \left(K_B \frac{\rho_{ecf} H^2}{R_0}\right)^{1-x} \cdot V_{WB}^{x} \quad (10)$$

where: x is a constant and typically approximately ⅓ or slightly less
$K_B$ is a whole of body shape factor
H is the subject height Similar for fluid levels more generally, this could be given by:

$$V = \left(K_B \frac{\rho H^2}{R}\right)^{1-x} \cdot V_{S}^{x} \quad (11)$$

where: ρ is the resistivity of the fluid
R is the impedance

For whole of body measurements, the dimensionless shape factor $K_B$ accounts for the facts that the human body is not a simple cylinder and that the measurement includes one arm, one leg and the trunk, but the remaining limbs and head are additional unmeasured mass. In one example, the shape factor for the whole body is calculated using the equation:

$$K_B = \frac{1}{H^2}\left[\left(\frac{L_l}{C_l^2} + \frac{L_t}{C_t^2} + \frac{L_a}{C_a^2}\right)(2L_a C_a^2 + 2L_l C_l^2 + 2L_t C_t^2)\right] \quad (12)$$

where: $K_B$ is the shape factor
H is the height of the subject
$L_l$ is the length of the leg
$L_t$ is the length of the torso
$L_a$ is the length of the arm
$C_l$ is the circumference of the leg
$C_t$ is the circumference of the torso
$C_a$ is the circumference of the arm Similarly, when applied to individual segments, this accounts for the fact that the segments are typically not strictly cylindrical in shape.

A provisional value for a whole body shape factor $K_B$ has been previously determined by to be around 4.3, and this is generally treated as a constant. However, this value was determined from army personnel data and is not representative of the general population. In addition, not all people will necessarily have the same shape, whilst differences are likely between ethnic groups, sexes and ages. The relative body proportions also vary for subjects of different height and weight.

Using a fixed shape factor therefore relies on the assumption that all subjects have their muscle and fat mass distributed in the same way, which is known to be incorrect. Accordingly, the above described process operates by determining a personalised shape factor based on dimensions of segments of the subject.

Whilst the dimensions could be measured for a subject's limb lengths and circumferences, in practice the time involved would be prohibitive in a clinical setting. Alternatively, other techniques could be used.

In one example, this is achieved by determining physical characteristics including a height, a weight, an age and a sex and determining the physical dimensions using physical characteristics. Thus, in this example, the shape factor is estimated using previously determined anthropometric relationships, and each subject's height and weight, which are already measured.

Alternatively, this could be achieved by capturing at least one image of the subject and measuring the physical dimensions from the at least one image. For example, this could be performed by determining a silhouette of the subject from the at least one image and measuring the physical dimensions from the silhouette.

In one example, when performing whole of body extracellular fluid indicator measurements, this is achieved by determining a whole of body impedance measurement, determining physical dimensions for segments including at least a torso, an arm and a leg, using the physical dimensions to determine a whole body shape factor and calculating the extracellular fluid indicator at least in part using the whole of body impedance measurement and the whole body shape factor.

A specific example of this will now be described with reference to FIGS. 10A to 10D and 11A and 11B.

In this example, at step 1,000 impedance measurements are performed at a number of different frequencies. To achieve this, an operator typically positions the electrodes 323, 324 on the subject S, and connects the leads 322, to allow the impedance measurements to be performed.

Figure 10A:
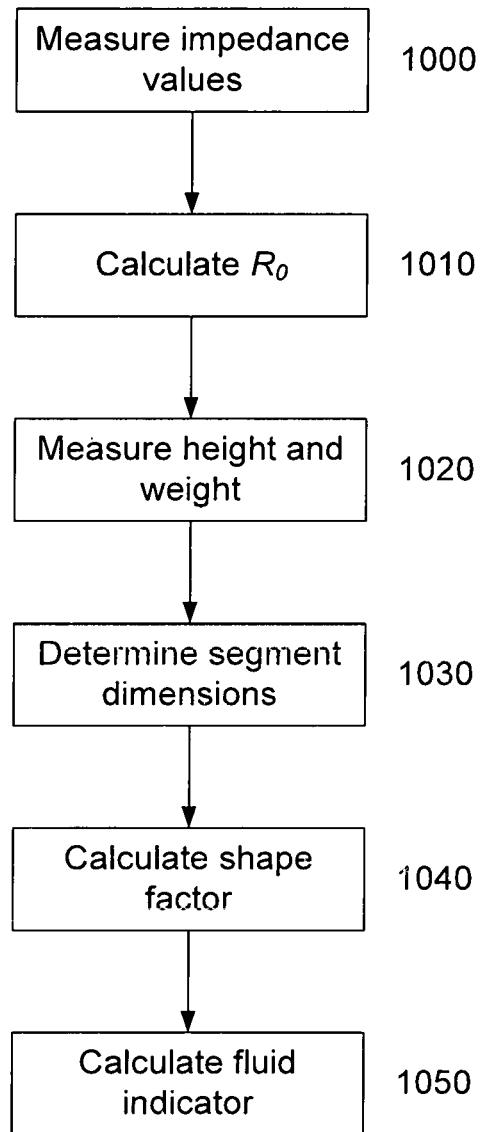
FIG. 10A is a specific example of a process for use in determining fluid levels within a subject.
Figure 10B:
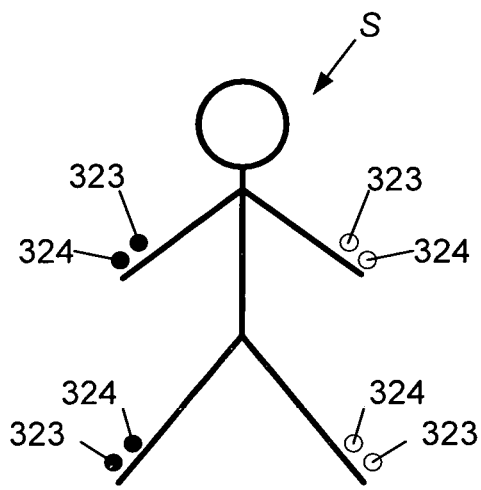
FIGS. 10B to 10E are schematic diagrams of examples of electrode positions for use in performing impedance measurements.
Figure 10C:
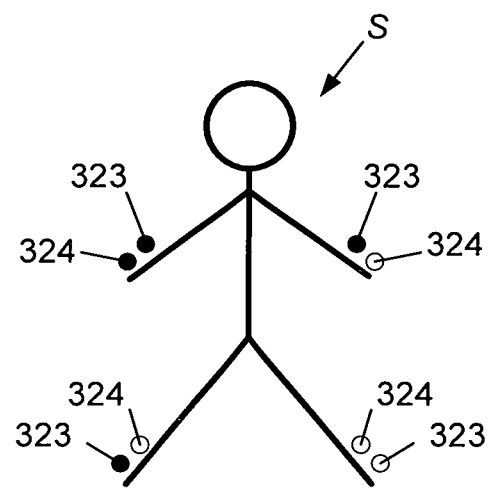
Figure 10D:
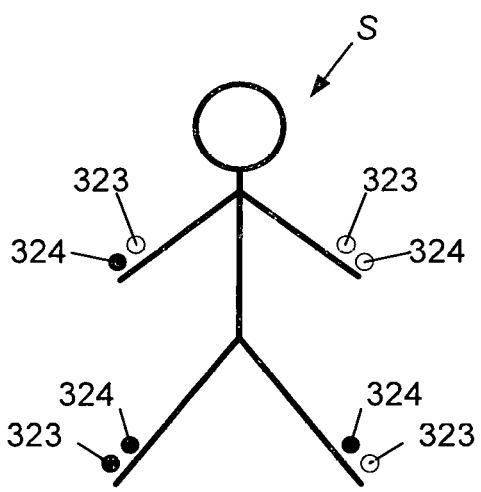
Figure 10E:
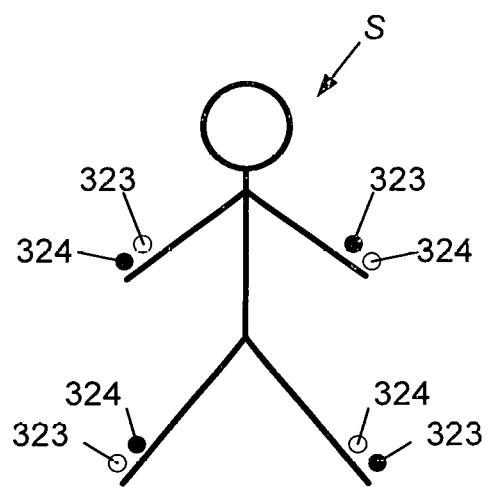

The general arrangement is to provide electrodes on the hand at the base of the knuckles and between the bony protuberances of the wrist, and on the feet at the base of the toes and at the front of the ankle. The configuration shown in FIG. 10B can then be used to allow whole of body measurements to be performed, whilst the configurations shown in FIGS. 10C, 10D and 10E can be used to allow the right arm, the right leg and torso to be measured respectively. Once electrodes are positioned, the operator activates the impedance measurement process, causing a sequence of drive signals to be applied to the subject at multiple frequencies. Corresponding sense signals are measured, allowing a value to be derived for the impedance parameter value $R_0$ at step 1010, using the techniques previously described. Alternatively, a single low frequency measurement can be performed and used to approximate the value of the impedance parameter value $R_0$, thereby reducing the complexity of the measurement process.

Following this, at step 1020, the height and weight of the subject are measured, and provided to the client device 330, for example using manual input techniques.

Figure 11A:
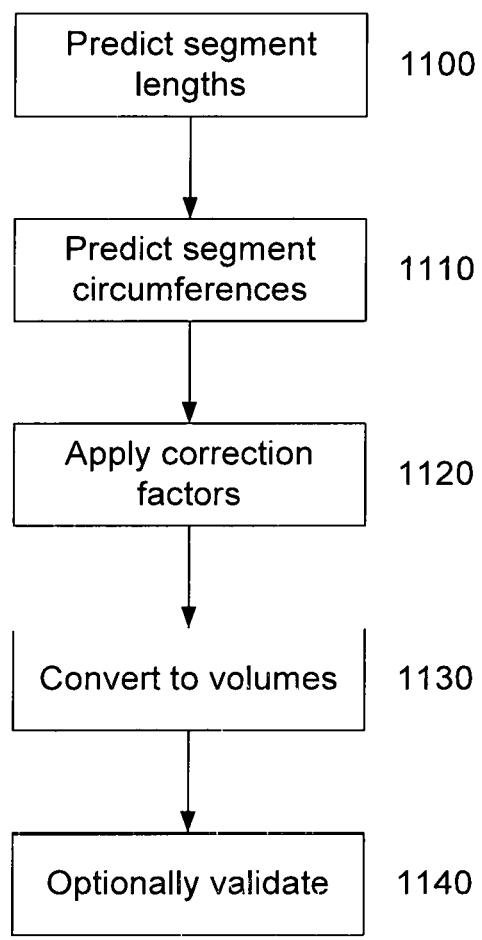
FIG. 11A is a flowchart of a first example of a process for determining segment dimensions.

Segment dimensions are then determined for the arm, torso and leg and a first example of this process will now be described with reference to FIG. 11A.

In this example, at step 1100, segment lengths for each of the arm, torso and leg are predicted using known anthropometric ratios, which relate the respective segment lengths to the height of the subject.

At step 1110, segment circumferences are predicted. In one example, this is achieved using the technique outlined in Heymsfield S B, Martin-Nguyen A, Fong T M, Gallagher D and Pietrobelli A 2008. Body circumferences: clinical implications emerging from a new geometric model. *Nutr. and Metab.* 5:24. This describes determined relationships between height, total body volume (approximately equivalent to weight), sex and age of subjects and the circumferences of the body segments at the upper arm, waist, hip, thigh and calf. In one example, this is given by:

$$\ln(circ) = k_0 + k_{age}\ln(age) + k_{V/H} \ln\left(\frac{V}{H}\right) \quad (13)$$

Where the constant coefficients are as in the table 1 below and V/H is the ratio of volume to height.

TABLE 1

| | | Arm | Waist | Hip | Thigh | Calf |
|---|---|---|---|---|---|---|
| Male | $k_{V/H}$ | 0.61 | 0.62 | 0.42 | 0.5 | 0.38 |
| | $k_{Age}$ | −0.052 | 0.1 | 0 | −0.1 | −0.04 |
| | $k_0$ | 4.2 | 4.63 | 4.96 | 4.8 | 4.1 |
| Female | $k_{V/H}$ | 0.62 | 0.61 | 0.49 | 0.54 | 0.33 |
| | $k_{Age}$ | 0.024 | 0.064 | 0 | −0.032 | −0.046 |
| | $k_0$ | 3.88 | 4.68 | 5.06 | 4.65 | 4.07 |

Following determination of circumferences, correction factors are applied at step 1120, to convert the segmental circumference to an equivalent cylindrical circumference. This is the circumference of a cylinder the same length as the body segment, and which has the same volume as the body segment. The correction factor will typically depend on factors such as sex, age or other parameters, and can be determined through analysis of a sample reference population.

Following this, volumes for the segments can be determined at step 1130, with these optionally being validated at step 1140 by calculating a volume error, using the subject weight and allowing for the head, hands and feet which are not included in the segments. A further test at this stage is to plot volume error against the shape factor $K_B$. If the prediction algorithms apply the wrong proportion of weight or volume to the different body segments, this is likely to lead to a $K_B$ error which is correlated with a volume error.

Figure 11B:
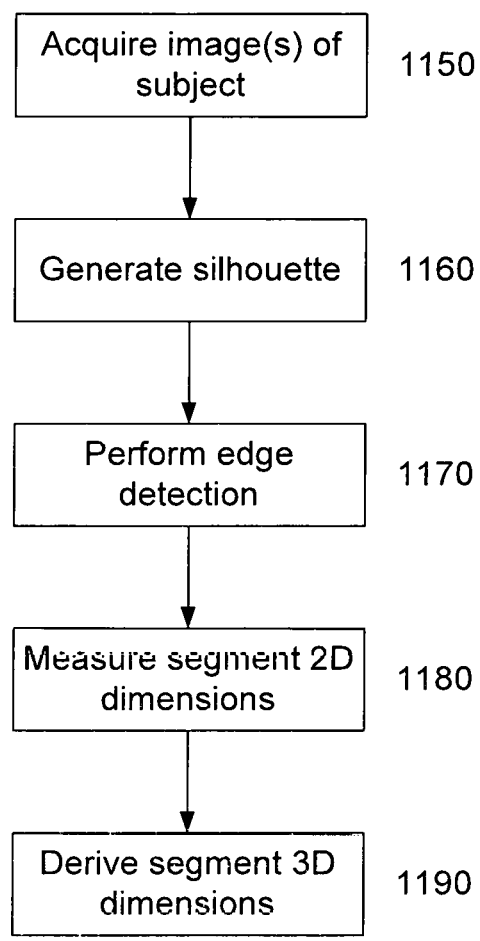
FIG. 11B is a flowchart of a second example of a process for determining segment dimensions.

As an alternative approach, shown in FIG. 11B, one or more images of the subject can be acquired at step 1150. This can be achieved by taking a photograph of the subject, or alternatively could be performed using other imaging modalities, such as DEXA (Dual-Energy X-ray Absorptiometry), 3D laser or optical scanning, or the like.

At step 1160, a silhouette is generated from the image(s), with edge detection and/or pattern recognition to be used to identify one or more landmarks, at step 1170. The landmarks correspond to defined locations on the body, which are used to derive 2D dimensions, which can then be extrapolated to 3D dimensions, including circumferences.

As part of this process the circumferences are then used to determine volumes, as in the previous example, allowing shape factors to be determined. As part of this process, multiple circumferences could be determined, for example by making multiple measurements along each body segment, allowing the volume to be more accurately determined, for example by integrating the circumferences along the length of the body segment.

Alternatively, the process could involve generating a 3D model following laser scanning and then measuring the values directly from the 3D model.

Once dimensions have been determined, at step 1040 this allows a body shape factor to be determined, using the equation (12) outlined above. Following this, at step 750, the client device 330 can determine an extracellular fluid indicator. In the case of whole body measurements, this can be performed using the equations (7) or (8), whereas for a segmental analysis, individual extracellular fluid indicators can be determined using the following equation:

$$SV_{ecf} = \left(K_S \frac{\rho_{ecf} L^2}{R_0}\right)^{1-x} \cdot V_S^x \quad (14)$$

where: $SV_{ecf}$ is the segmental extracellular fluid volume
$K_S$ is the segmental shape factor
$V_S$ is the segment volume
$\rho_{ecf}$ is the resistivity of extracellular fluid
L is the segment length
$R_0$ is the impedance at zero frequency
x is a constant Similar for fluid levels more generally, this could be given by:

$$SV = \left(K_S \frac{\rho L^2}{R}\right)^{1-x} \cdot V_S^x \quad (15)$$

where: SV is the segmental fluid volume
ρ is the resistivity of the fluid
R is the impedance Thus, the above described technique allows body composition estimates to be made using a personalised $K_B$ value.

Thus, it will be appreciated that whilst the above described example has focused on the application to whole body extracellular measurements, similar techniques could also be applied to segmental extracellular fluid measurements. In this example, the approach typically includes determining a segmental impedance measurement for at least one segment, determining physical dimensions for the at least one segment, using the physical dimensions to determine a segmental shape factor and calculating the extracellular fluid indicator at least in part using the segmental impedance measurement and the segmental shape factor.

In any event, it will be appreciated that the above described approach allows analysis of measured impedances, which can in turn be used to determine body composition parameters. These techniques utilise information regarding physical characteristics of the subject in order to analyse the impedance measurements and derive the body composition information, allowing this information to also be used when ascertaining the reference signatures as described above.

Figure 12:
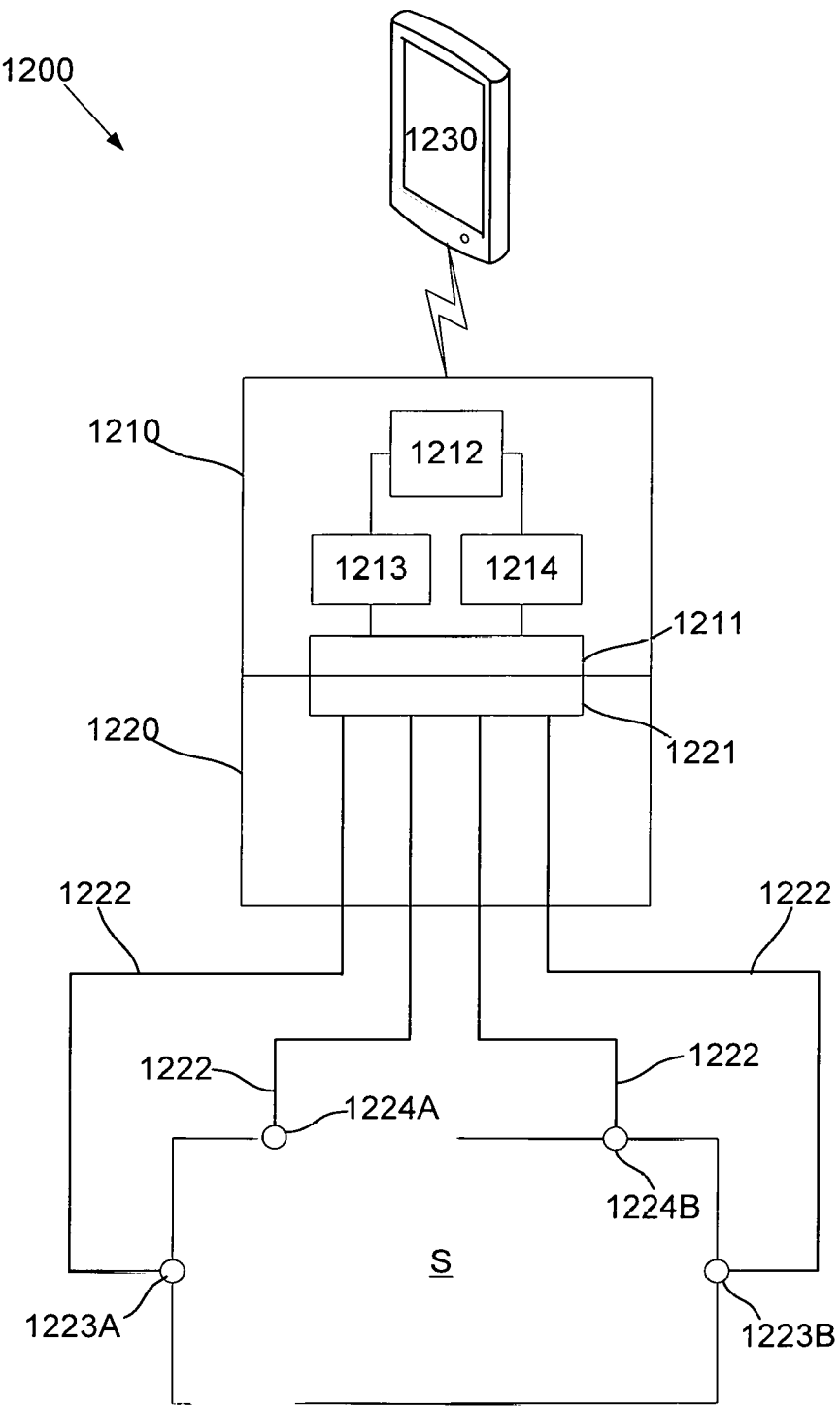
FIG. 12 is a schematic diagram of an example of an impedance measuring system.

The above described process has been described as being performed using a measuring unit including a measuring device 310 coupled directly to electrodes. However, alternative arrangements can be used and a further example of a measuring unit will now be described with reference to FIG. 12.

In this example, the measuring unit is similar to that described above with respect to FIG. 3, and similar features will not therefore be described in detail. However, in this example, the measuring unit includes a measuring device 1210 including a first connector 1211 electrically connected to at least the at least one sensor 1214 and the at least one signal generator 1213, and a separate connectivity module 1220, including a connectivity module housing and a second connector 1221 electrically connected to the electrodes 1223, 1224.

In use the measuring device 1210 is connected to the connectivity module 1220 by interconnecting the first and second connectors 1211, 1221 so first electrodes 1223 are electrically connected to the at least one signal generator and second electrodes 1224 are electrically connected to the at least one sensor, thereby allowing a drive signal to be applied to the subject via the first electrodes 1223 (referred to generally as drive electrodes) and allowing the response signal to be measured via the second electrodes 1224 (referred to generally as sense electrodes) so that the at least one impedance measurement can be performed.

In the above described arrangement, a separate measuring device 1210 and connectivity module 1220 are used, allowing a single type of measuring device 1210 to be configured for use with multiple different types of connectivity module 1220. This in turn enables a range of different impedance measurements to be performed using different configurations of connectivity module. In this regard, different electrode arrangements 1223, 1224 may be required for performing different types of impedance measurement, and so the provision of a common measuring device, and different types of connectivity module allows a single measuring device to be used in a wider range of circumstances than would be possible for a single integrated device.

For example, the connectivity module 1220 could include stand-on plates and hand grip electrodes for use in measuring aspects of a subject's body composition, whilst adhesive electrodes positioned on the wrist and ankles might be preferred for oedema detection, or the like. In this instance, by allowing a common measuring device to be selectively connected to different connectivity modules, this allows the most suitable electrode configuration to be used, whilst allowing a common measuring device design to be used, which can reduce overall hardware requirements and allow for greater efficiencies in manufacture.

Furthermore, in one example, the measuring device 1210 can be adapted to sense the type of connectivity module 1220 to which it is connected, thereby at least partially controlling the impedance measurement process based on the connectivity module currently being used.

Figure 13:
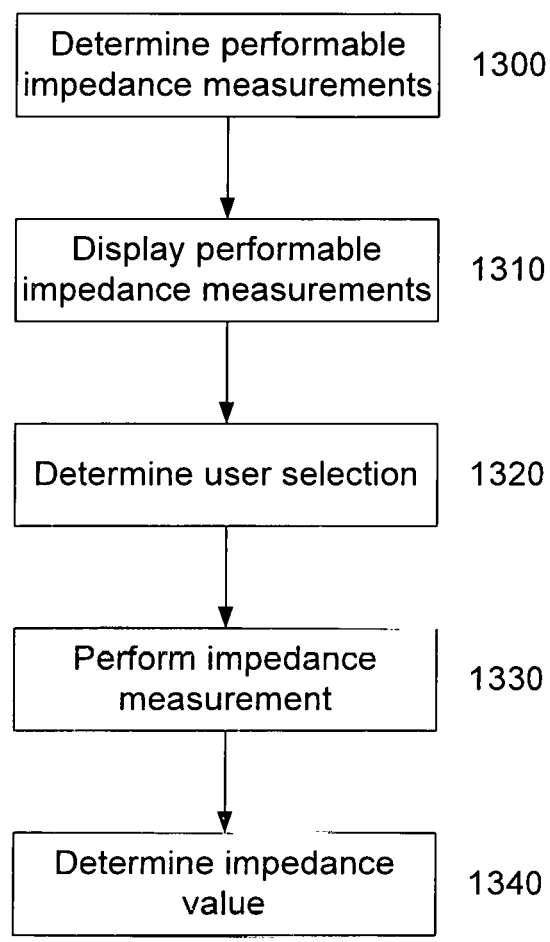
FIG. 13 is a flowchart of an example of an impedance measuring process.

An example of this, will now be described with reference to FIG. 13.

In this example, at step 1300, the measuring device processor 1212 determines a connectivity module type. This can be achieved in any suitable manner, depending on the preferred implementation and could be based on a configuration of connections between the connectors 1211, 1221, electrical characteristics or properties of components within the connectivity module, stored identifiers, or the like.

At step 1310, the connectivity module type is used to determine the impedance measurements that can be performed using the respective connectivity module 1220. This can be performed by the measuring device processor 1212, or alternatively could be performed by a client device 1230 in communication with the measuring device processor 1212. In any event, different connectivity module types could be associated with respective types of impedance measurement, for example based on the configuration of electrodes and/or any other components provided therein, such as voltage/current buffers or the like. Thus, information regarding the connectivity module type can be used to determine the impedance measurements that can be performed, allowing operation of the system to be controlled accordingly.

Prior to a measurement being performed, the first and second electrodes 1223, 1224 are positioned on the subject to allow one or more signals to be injected into the subject S, and allowing a response signal to be measured.

Once positioned, at step 1320, the measuring device processor 1212 controls the at least one signal generator 1213 and the at least one sensor 1214, allowing the impedance measurements to be performed at step 1330, with impedance values being determined at step 1340.

A number of further features will now be described.

In one example, the measuring device processor determines a connectivity module type of the connected connectivity module and in accordance with the determined connectivity module type, causes the at least one impedance measurement to be performed or processes a measured response signal to determine at least one impedance value indicative of a measured impedance. Accordingly, this allows the impedance measurement or analysis processes to be controlled based on the connectivity module type.

The connectivity module type can be determined in any suitable manner. In one example, this is determined using one or more of a configuration of connections between the first and second connectors or a configuration of the second connector. For example, the first and second connectors can include a plurality of individual connections, with the connectivity module type being determined based at least in part on connections between individual connections of the second connector, created for example using jumpers or other similar arrangements. Alternatively, this could be based on a property of an electrical component electrically connected to the second connector, such as the resistance of a resistor coupled between respective connections on the second connector. Thus, the connectors could be configured, either based on respective interconnections, or through components coupled thereto, so that the connectivity module type can be determined automatically based on the configuration of the connectors.

Alternative mechanisms could also be used for determining a connection module type, such as by having the measuring device include a contact switch that is selectively actuated by the connectivity module housing when the measuring device and connectivity module are connected, so that a different switch position or different switch is actuated for different connectivity module types.

Additionally, and/or alternatively, the measuring device processor could determine an identifier associated with the connectivity module and determine the connectivity module type using the identifier. In this example, the connectivity module could include a memory, with the measuring device processor retrieving the identifier from the memory via a wireless connection or via the first and second connectors. The identifier could be in the form of a unique alphanumeric code or the like, and could include a portion that is indicative of a connectivity module type, and an additional serial number or the like, allowing not only the module type to be determined, but also allowing each module of a given type to be distinguished, which can be useful for calibration or tracking individual modules.

As a further alternative, instead of determining a connectivity module type, the measuring device processor could retrieve instructions from a memory in the connectivity module, via a wireless connection or the first and second connectors and then cause impedance measurements to be performed in accordance with the instructions. In this instance, instructions corresponding to measurements that can be performed are stored on the connectivity module itself, allowing these to be simply accessed and used as required.

Additionally, as mentioned above, the measuring device processor may determine the connectivity module type and then pass this information to a remote processing system, such as a client device, allowing the client device to determine the impedance measurements that can be performed in a similar manner.

As previously mentioned, the measuring device processor typically determines at least one impedance value indicative of at least one measured impedance using an indication of at least one drive signal applied to the subject and an indication of at least one measured response signal. Additionally however, the measuring device processor can also take into account calibration data stored in a memory. In this regard, the inherent electrical properties of the measuring device 1210 and/or the connectivity module 1220 can have an impact on the magnitude and/or phase of signals that are measured for a given impedance. For example, longer leads 1222 between the electrodes 1223, 1224 and the second connector 1221, can introduce additional resistances, leading to different voltages being recorded for the same impedance. Accordingly, calibration of the measuring device 1210 and/or connectivity module 1220 may be required in order to ensure that signals are accurately interpreted. Such calibration data can be established through measurement of reference impedances during a calibration process, and is taken into account when calculating the impedance, for example by modifying the resulting impedance or the phase and/or magnitude of measured signals prior to the impedance being measured.

In one example, the calibration data includes first calibration data specific to the measuring device and second calibration data specific to the connectivity module. In this instance, the measuring device processor 1212 might determine the calibration data to be used based on a connectivity module type and/or a connectivity module identifier, so that the calibration data is specific to the type and/or particular connectivity module being used.

In one example, the measuring device processor 1212 selects one of a number of calibration data sets stored in a memory, allowing the measuring device processor 1212 to select and use the most appropriate calibration data, depending on the connected connectivity module and/or the impedance measurement being performed. In this regard, it will be appreciated that different calibration data might be required for example for high versus low frequency measurements.

The first and second connectors can be of any appropriate form but typically include multi-pin plug and a corresponding multi-pin socket connectors. In one example further physically separate connectors could also be provided, for example to allow for connection of different components. Thus, the first and second connectors could be used to connect the signal generator and/or sensor to the electrodes, with connections for indicators, such as LEDs, speakers or the like, being via different connectors, which can help avoid interference or the like.

The measuring device housing and connectivity module housing are typically configured to physically interconnect when the measuring device is connected to the connectivity module, for example using a clip-fit, friction-fit, interference-fit, magnetic coupling or the like.

The electrodes can be mounted on the connectivity module housing and/or coupled to leads extending from the connectivity module housing. It will be appreciated that this will depend on the intended usage, and specific examples will be described in more detail below.

In one example, the electrodes form part of at least one electrode sheet, which can include a substrate and conductive material defining each electrode, the conductive material being either impregnated in the substrate and/or printed on a surface of the substrate. In this example, the electrode sheet can include a connection tab extending from the substrate that allows a lead connector to be electrically coupled to the electrodes. In this regard, the tab can have electrical surface tracks provided thereon, allowing the tracks to electrically connect to contacts on the lead connector allowing for ease of connection.

In one example, the connectivity module 1220 can include little more than the connector 1221 and connections, such as leads 1222, to the electrodes. However, alternatively, the connectivity module can include additional components, such as at least one buffer circuit coupled to each electrode, which is particularly important for high frequency operation. Thus, for example, the signal generator and sensor provided in the measuring device could be in the form of an DAC and ADC respectively, with respective amplifiers being provided in the connectivity module. It will be appreciated from this that power may be required by the connectivity module in which case a power supply such as a battery could be provided in the connectivity module. This could be a separate power supply to that used in the measuring device, or alternatively a common power supply could be used with power being transferred between the measuring device and connectivity module via the first and second connectors as required.

In one example, the measuring device includes a respective signal generator and/or sensor for each electrode. For example, for a four channel device, the measuring device can include four signal generators, each being electrically connected to a respective drive electrode and four sensors, each being electrically connected to a respective sense electrode and wherein the measuring device processor selectively activates the at least one signal generators and sensors to thereby allow a respective impedance measurement to be performed.

However, alternatively, the measuring device 1210 includes a switching unit, such as a multiplexer, for selectively electrically connecting the at least one signal generator and the at least one sensor to the first connector thereby allowing the at least one signal generator and the at least one sensor to be selectively connected to different electrodes. In this instance, the measuring device processor 1212 controls the switching unit to thereby selectively electrically connect the at least one signal generator and the at least one sensor to respective electrodes thereby allowing a respective impedance measurement to be performed. It will also be appreciated that such a switching unit could alternatively be provided in the connectivity module, although this is generally undesirable as it leads to additional complexity of the connectivity module 1220.

The measuring device 1210 can be controlled remotely using a processing system, such as the client device 1230. Nevertheless, the measuring device 1210 typically includes at least some form of minimal input/output device, to allow for user interaction. In one example, this includes an input button that activates the measuring device and/or causes at least one impedance measurement to be performed. The measuring device can also include an indicator, such as an optical indicator, a multi-colour LED, speaker or the like, which can be used to indicate completion of an impedance measurement, performing of an impedance measurement or connection to a connectivity module and/or processing system.

The measuring device 1210 typically includes an interface, such as a wireless interface, for example Bluetooth or the like, that allows the measuring device processor to communicate with a processing system using at least one of wired and wireless communications.

In this case, the system 1200 can include a processing system 1230 that determines at least one impedance measurement to be performed, causes the measuring device 1210 to perform the at least one impedance measurement and receives an indication of at least one impedance value from the measuring device, the at least one impedance value being indicative of a measured impedance. In one example, the measuring device processor 1212 can communicate with the processing system 1230 to determine the at least one impedance measurement to be performed and/or provide the indication of at least one impedance value to the processing system 1230. Thus, this allows the processing system 1230, which can be in the form of a client device such as a computer system, smartphone, tablet or the like, to act as a user interface, allowing the measuring device to be controlled and allowing results of the impedance measurement process to be reviewed. This in turn reduces the hardware requirements of the measuring device 1210, whilst still allowing a range of different functionality to be implemented. The processing system 1230 could be remote from the measuring device and connectivity module, or alternatively could be integrated into the connectivity module, depending on the preferred implementation.

In one example, the processing system 1230 can determine an impedance measurement process to be performed, the impedance measurement process including a sequence of impedance measurements and cause the measuring device processor to perform the sequence of impedance measurements. This allows the processing system to be used to cause a complex sequences of impedance measurements to be performed, based for example on sequences stored locally on the processing system. This allows the system to be configured for particular circumstances, whilst allowing the measuring device 1210 to be generic in terms of functionality, thereby minimising hardware requirements.

The processing system can also process the at least one impedance measurement to determine at least one indicator indicative of a biological state of the subject. This can be used for example to create an indicator that is indicative of a status of the subject, such as a fluid level, body composition parameter, or the like, making results of the impedance measurement easier for users, such as clinicians, to understand.

In one example, the processing system displays a user interface allowing a user to select at least one impedance measurement to be performed, select an impedance measurement process to be performed, the impedance measurement process including a sequence of impedance measurements, view at least one impedance measurement and view at least one indicator indicative of a biological state of the subject. However, this is not essential, and any suitable approach can be used.

In one example of the above described arrangements, the measuring device processor 1212 can determine at least one performable impedance measurement based on a connectivity module type of a connected connectivity module and provide an indication of this to the processing system, which then displays an indication of the at least one performable impedance measurement to a user, determines a selected performable impedance measurement in accordance with user input commands and causes the measuring device to perform the selected performable impedance measurement. Thus, the measuring device 1210 can determine the impedance measurements that can be performed based on the connected connectivity module, with this information being used by the processing system 1230 to display available impedance measurement processes, so that one of these can be selected by the user. It will also be appreciated that a similar technique can be used to select the type of analysis that can be performed allowing indicators indicative of a biological status, such as body composition, fluid levels or the like, to be determined.

Figure 14A:
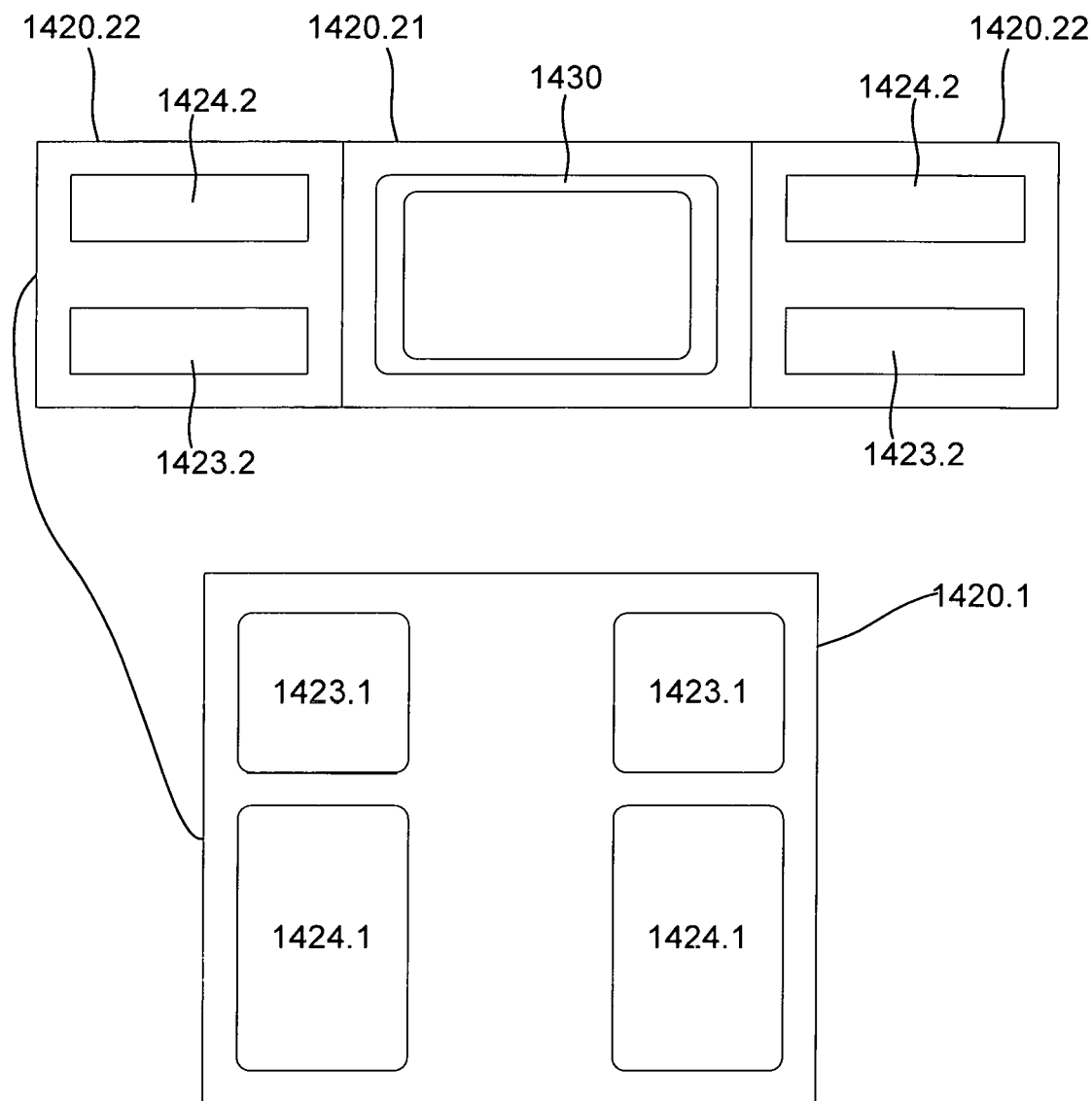
FIG. 14A is a schematic diagram of a specific example of an impedance measuring system.
Figure 14B:
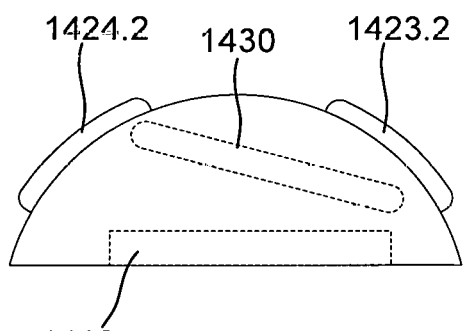
FIG. 14B is schematic end view of a second housing of the connectivity module of FIG. 14A.

A specific example connectivity module is shown in FIGS. 14A and 14B.

In this example, the connectivity module 1420 includes first and second housings 1420.1, 1420.2. The first housing 1420.1 has a form factor similar to a set of scales, and includes two spaced pairs of foot drive and sense electrodes 1423.1, 1424.1 forming footplates, or laminar electrode sheets, on which a user can stand. The second housing 1420.2 is an elongate housing having three portions along its length, with a central rectangular portion 1402.21 positioned between two outer semicylindrical portions 1420.22. In this example, the outer semicylindrical portions 1420.22 support curved electrode plates 1423.2, 1424.2 or electrode sheets, mounted on opposing sides of the body allowing the user to place their palms and fingers on the plates 1423.2, 1424.2. In this regard, the curvature of the surface assists with comfort and ensures good physical and hence electrical contact between the user's hands and the electrodes. Meanwhile the central portion can be used to support the measuring device 1410, and also optionally a client device 1430, such as a tablet or the like, which can be used to control the measurement process as will be described in more detail below.

It will be appreciated however that a wide variety of connectivity modules could be provided, with these being used in different circumstances to allow respective types of impedance measurement to be performed, whilst still using a common measuring device.

Figure 15A:
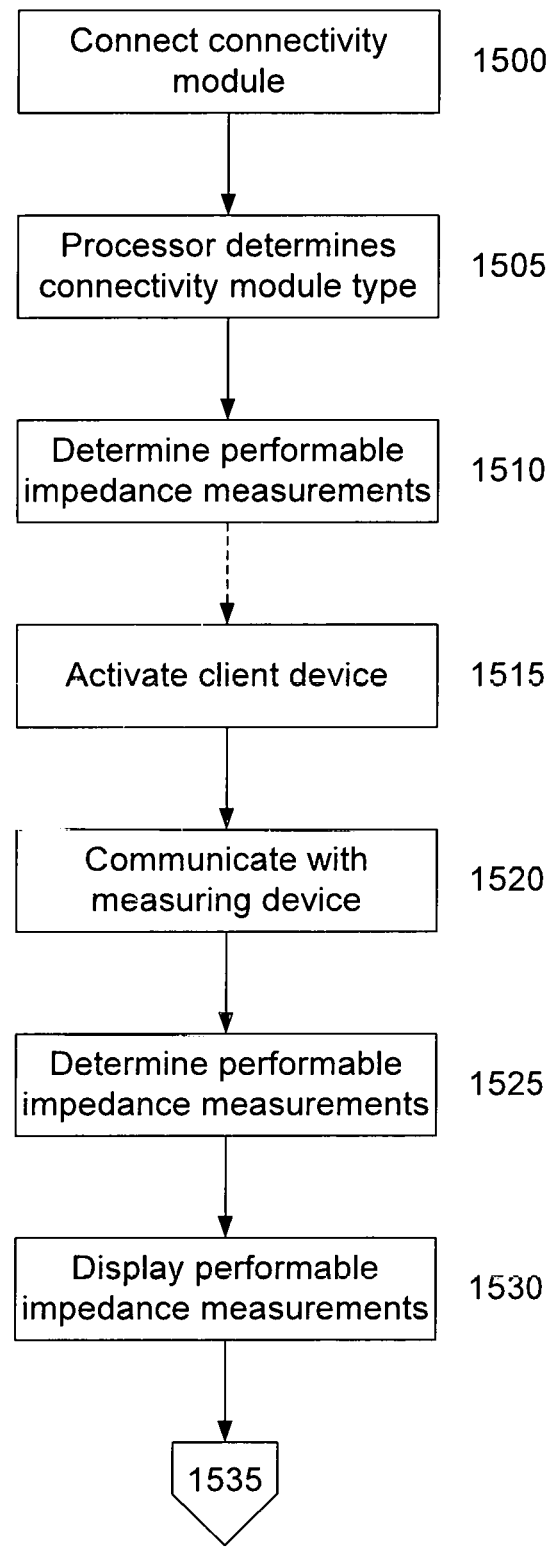
FIGS. 15A to 15C are a flowchart of a further example of an impedance measuring process; and, FIG. 16 is a schematic diagram of a further specific example of an impedance measuring system.
Figure 15B:
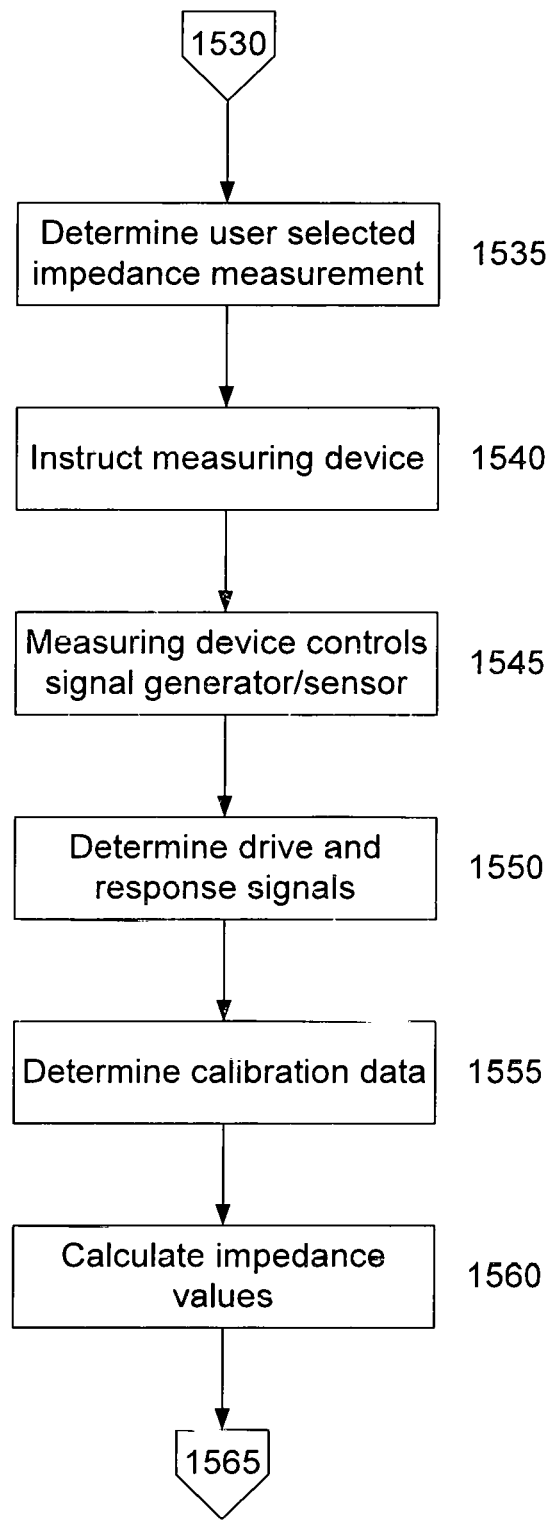
Figure 15C:
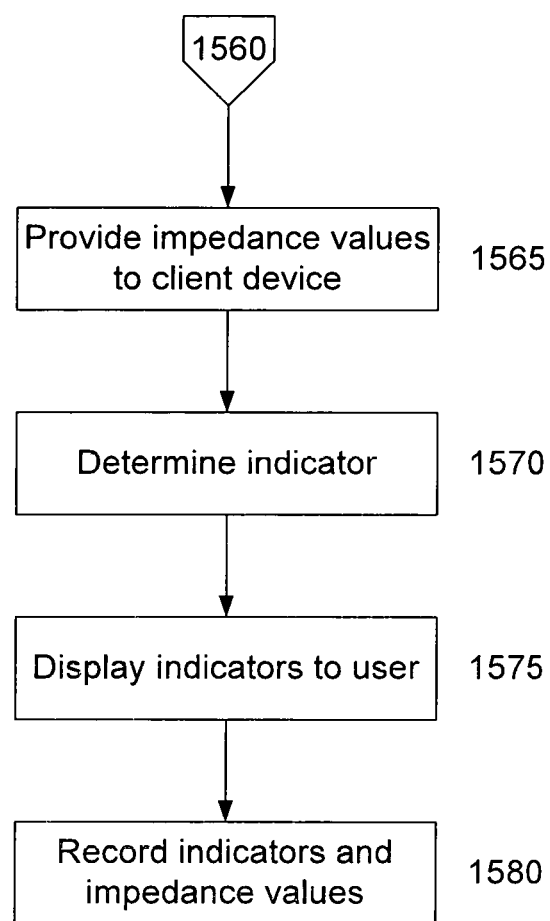

A further example of an impedance measurement process will now be described with reference to FIGS. 15A to 15C.

In this example, at step 1500 the measuring device 1210 is initially connected to a connectivity module 1220, and activated, causing the measuring device processor 1212 to determine a connectivity module type of the connectivity module 1220 at step 1505. This is typically performed by having the measuring device processor determine a connectivity module identifier or the like, allowing the measuring device processor to determine performable impedance measurements at step 1510. In this regard, the measuring device 1210 can store a list of performable impedance measurements that can be performed for each type of module in onboard memory, allowing an indication of performable impedance measurements to be retrieved based on the connectivity module type. However, alternatively, the connectivity module type could be provided to the client device 1230, allowing this to be performed by the client device 1230.

At step 1515, the client device 1230 is activated, with relevant software being activated, allowing the client device 1230 to commence communicating with the measuring device 1210 at step 1520. As part of this process, the measuring device and client device may need to be paired, for example undergoing a Bluetooth pairing process, or the like, depending on the manner in which the client device 1230 and measuring device communicate. Alternatively a particular client device 1210 previously paired with the client device 1230 may need to be identified from a list of available devices, as will be appreciated by persons skilled in the art.

At step 1525, the client device 1230 determines the performable impedance measurements from the measuring device 1210, or receives an indication of the connectivity module type, allowing the performable impedance measurements to be determined locally. In any event, an indication of the performable impedance measurements is then displayed to a user at step 1530, for example in the form of a list of impedance measurement processes.

The user selects a performable impedance measurement at step 1535, causing the client device 1230 to instruct the measuring device 1210 to perform the impedance measurements at step 1540. This can include providing the measuring device 1210 with an indication of particular impedance measurements to be performed, or could include providing instructions regarding the control of or settings for the signal generator, sensor and any switches. Additionally and/or alternatively, this could include uploading soft or firmware to the measuring device, allowing the measuring device 1210 to operate as required.

At step 1545, the measuring device processor 1212 controls the signal generator/sensor 1213, 1214, determining corresponding drive and response signals, applied or measured via respective drive and sense electrodes 1223, 1224, at step 1550. The measuring device processor 1212 then determines calibration data at step 1555, with this typically being stored locally and accessed based on either the connectivity module type and/or connectivity module identifier. In this regard each type of connectivity module will typically have different electrical properties and these will need to be taken into account when performing impedance measurements. This is achieved by measuring drive and response signals for standardised electrical components with this then being used to generate calibration data which can be used in calculating impedance measurements. This could be performed for each type of module, and/or for each individual connectivity module, depending for example of the level of accuracy required for the calculated impedance values.

In any event, the calibration data is used together with the indication of the drive and corresponding response signals to calculate impedance values at step 1560, for example by modifying the measured drive and response signals to take into account device characteristics, and then using the modified signals to calculate the impedance.

Once impedance values have been calculated for each measurement performed, an indication of the impedance values being provided to the client device 1230 at step 1565, allowing these to be used by the client device to determine one or more indicators at step 1570. This process can involve calculating impedance parameter values, such as $R_0$, $R_x$, or the like and then using these values to determine indicators, such as fluids levels including levels of extracellular and intracellular fluid, body composition parameters, such as fat free mass, or the like.

The determined indicator(s) and/or impedance values can then be displayed to the user at step 1575, via a suitable user interface with the indicators and impedance values being optionally stored at step 1580, for example by transferring these to the server 250 for storage in the database 251.

Accordingly, it will be appreciated that the above described arrangement allows the impedance measurement procedure to be controlled via a client device, such as a smartphone or tablet. This allows general processing of impedance measurements and control of the system to be performed using generic hardware, without unduly adding to the cost of the impedance measuring system.

In the above described arrangements, a single configuration of measuring device is adapted to be used with connectivity modules that provide onward connectivity to the subject. Different types of connectivity module can be used with the same measuring device, with the nature of the connectivity module being used to control the impedance measuring processes that can be performed. This allows a user to obtain a single measuring device and then use this with different connectivity modules, allowing different measurements to be performed. This reduces the complexity of the measuring device, and allows a single configuration of measuring device to be used in wide range of scenarios. Additionally, this allows users to only acquire connectivity modules that are relevant to measurements that are to be performed, avoiding the need to acquire unnecessary hardware. Finally, this also allows the connectivity modules to be customised for the particular measurements that are to be performed, which in turn helps ensure the electrode configuration is optimised for the particular measurements being performed.

In the above described arrangements, the measuring device is provided in a measuring device housing that is separate to the connectivity module housing. This is beneficial in terms of facilitating use of a single measuring device with multiple different connectivity modules, particularly in terms of allowing for measuring device handling to be performed when attaching or detaching the measuring device and connectivity modules, without potential to damage components of the measuring device.

However, it will be appreciated that this is not essential, and alternatively, the measuring device could be provided within the connectivity module housing, and hence not require a separate measuring device housing. In this instance, the connectivity module housing could include a door, cover, lid or other opening, that provides access to the inside of the connectivity module, and the second connector provided therein. This allows the measuring device to be inserted into the connectivity module housing and coupled to the second connector, in a manner substantially similar to that described above, albeit with the measuring device contained entirely within the connectivity module housing.

For example, the measuring device could include a circuit board, having the relevant components and first connector mounted thereon. This could be supported internally within the connectivity module, either through physical engagement between the first and second connectors, or through cooperation with a separate bracket or other mounting. Thus, it will be appreciated that this arrangement could be analogous to the manner in which a card, such as a graphics card or RAM is installed in a computer system housing through attachment to a motherboard, with the measuring device corresponding to the card, and the connectivity module the computer system and motherboard.

In this latter arrangement, it would be typically although not essential for the measuring device to be mounted in a single connectivity module, as opposed to being used interchangeably with different connectivity modules, to thereby ensure components of the measuring device are not damaged. Nevertheless, this would still allow for common measuring devices to be used with a wide range of different connectivity modules, thereby reducing manufacturing complexity and requirements, whilst still allowing a wide range of functionality to be achieved.

Figure 16:
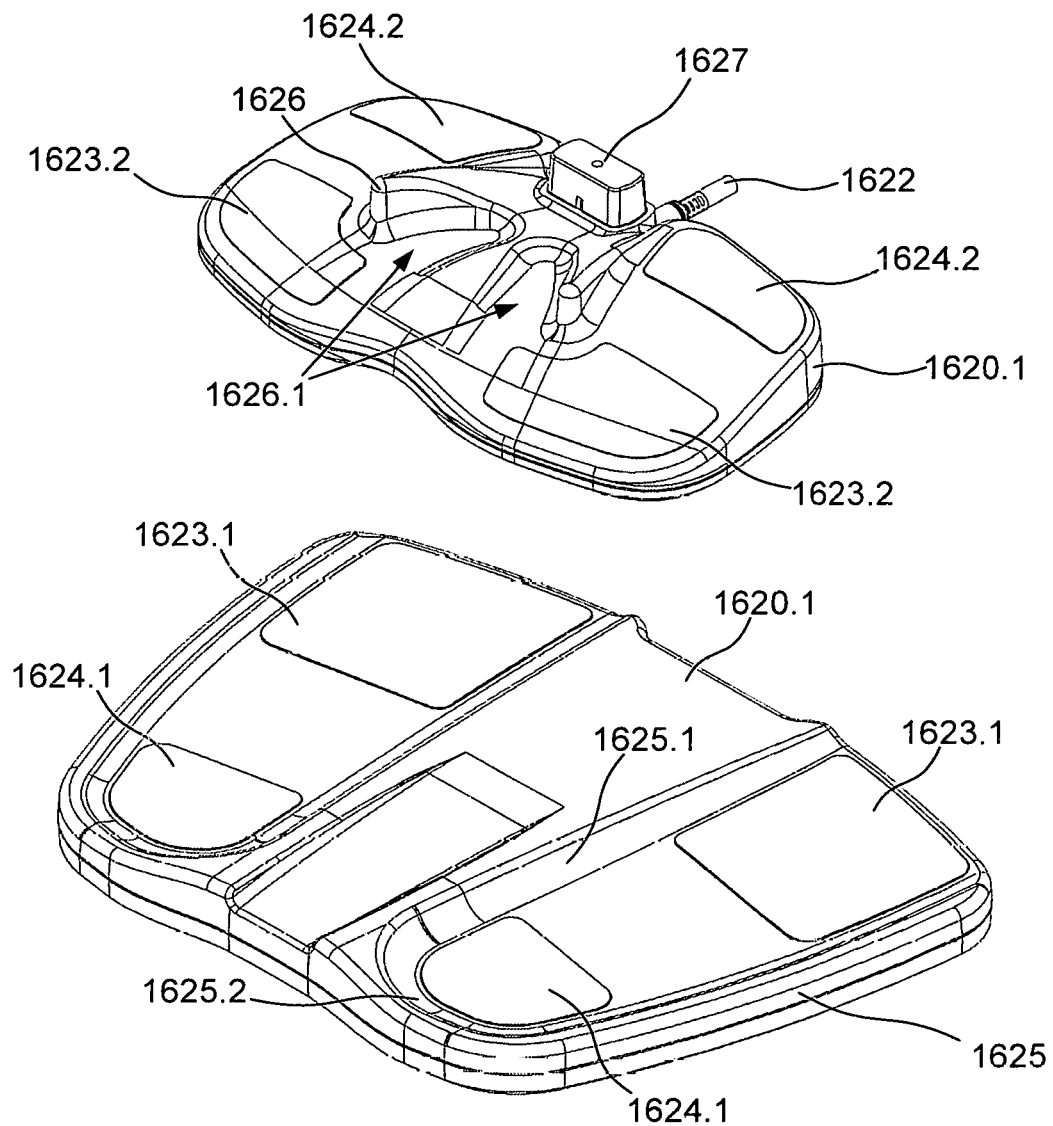

An further example of a physical construction of the measuring device is shown in FIG. 16.

In this example, the measuring device includes first and second housings 1620.1, 1620.2. The first housing 1620.1 has a form factor similar to a set of scales, and includes a generally rectangular body having two spaced pairs of foot drive and sense electrodes 1623.1, 1624.1 formed from spaced apart metal plates provided on an upper surface, thereby forming footplates on which a user can stand. The second housing 1620.2 has a generally rectangular body having two spaced pairs of hand drive and sense electrodes 1623.2, 1624.2 formed from spaced apart metal plates provided on an upper surface, thereby forming handplates on which a user can rest their hands.

The first housing 1620.1 includes a raised section 1625, defining a lip 1625.1 extending at least partially around each pair of foot drive and sense electrodes to thereby guide positioning of a subject's foot relative to the foot drive and sense electrodes in use. In particular, the raised lip 1625.1 includes a rear portion 1625.2 configured to engage at least a heel of the user. A similar effect is achieved for the second housing by having a raised portion 1626 positioned between each pair of hand drive and sense electrodes, the raised portion defining thumb recesses 1626.1 to thereby guide positioning of a subject's thumbs, with the crook of the thumb engaging the raised portion, and hence hands relative to each pair of hand drive and sense electrodes in use.

In this regard, it will be appreciated that whilst this will still allow for some minor variation in positioning between different individuals, for example due to different feet and hand sizes, this helps ensure that any given user's hands and feet are provided at a consistent position relative to the drive and sense electrodes each time the apparatus is used. This provides reproducible positioning, which in turn reduces variations between successive measurements that could be caused by changes in hand or foot position.

This arrangement allows the unit to be used by having the user stand on the first housing, or alternatively sit on a chair, with their feet resting on the foot drive and sense electrodes. The user can then place their hands on the hand drive and sense electrodes on second housing, which can be supported by a desk or table in a seated arrangement, or by a stand or other support for a standing arrangement.

The use of two housing containing separate electrodes, therefore allows impedance measurements to be performed in a variety of circumstances, and in particular allows measurements to be performed in either seated or standing arrangements, which is important in ensuring the system can be used by individuals having restricted physical capabilities. Additionally, the use of metal plate electrodes provided in a housing allows the system to be readily used, and avoids the need for preparation, such as cleaning of tissue surfaces or removal of hair, to allow wet electrodes to be applied to the skin.

Accordingly, it will be appreciated that the above described approach allows impedance measurements to be used in a manner akin to other vital signs. In particular impedance measurements can be used to enable or facilitate diagnosis of a wide range of different body states.

This could be performed independently, but is more typically performed in conjunction with measurement of other body parameters, such as vital signs to provide enhanced discriminatory capabilities.

Whilst this could be performed in an ad-hoc manner, more preferably this is achieved using a standardised approach performed in a range of different locations and circumstances, allowing impedance indicators to be measured for a wide variety of physical characteristics and body states. The data can then be aggregated centrally and mined in order to derive reference signatures, each of which defines a combination of impedance and/or other body parameter indicators that are unique to a particular body state for a given set of physical characteristics. Subsequently, impedance and optionally other body parameter indicators can be measured for subjects, and then compared to the reference signatures, allowing a likelihood of the subject having a respective body state to be quantified in the form of a body state indicator, which can be an indication of the likelihood of the subject having one or more body states. This information can then be used by clinicians, in order to assist clinicians in making a clinical diagnosis of body states.

In one particular example, a system can be provided for determining a body state indicator for a biological subject. The system includes a number of measuring systems, each measuring system being capable of performing impedance measurements on a user and having a measuring device and a client device.

The measuring device includes at least one signal generator electrically connected to drive electrodes to apply a drive signal to a user, at least one sensor electrically connected to sense electrodes to measure a response signal in the user and a measuring device processor, which controls the at least one signal generator, receives an indication of a measured response signal from the at least one sensor and generates measurement data indicative of at least one measured impedance value.

The client device is in communication with the measuring device and receives the measurement data, generates user data indicative of the measurement data and a user identifier associated with the user and communicates the user data via a communication network to one or more one processing devices.

The one or more processing devices use the user data to generate reference signatures based on measurements from reference individuals and then subsequently analyse user data from a subject to generate an indicator indicative of a body state.

The reference signatures are generated by obtaining user data for a plurality of reference individuals from one or more of the number of measuring systems, via the communications network. The user data is used to determine reference data including at least one reference impedance indicator obtained from user data by performing at least one impedance measurement on the reference individual, a reference body state indication indicative of any body states associated with the reference individual and reference characteristic data indicative of one or more physical characteristics of the reference individual. This can be based on the user data, and/or retrieved from previously stored data using the user identity.

The reference data is then analysed for the plurality of reference individuals to establish the one or more reference signatures, each reference signature being indicative of at least one reference impedance indicator associated with a respective body state for respective physical characteristics.

When a subject is to be analysed this can be performed by obtaining user data for the subject from one of the number of measuring systems and then using this to determine subject data. The subject data includes subject characteristic data indicative of one or more physical characteristics of the subject and at least one subject impedance indicator derived from at least one measured impedance value for the subject.

The subject data is then analysed using the reference signatures and the subject characteristic data, with at least one body state indicator being generated in accordance with the analysis.

Thus, this allows measurements from a plurality of reference individuals to be used to establish reference signatures, which are then used to analyse measurements of a subject.

The reference/subject impedance indicators can include at least one impedance value measured for at least one body segment of the reference individual/subject, at least one impedance parameter value derived from at least one impedance value measured for at least one body segment of the reference individual/subject, or a fluid level indicator indicative of fluid levels in at least one body segment of the reference individual/subject, the fluid level indicator being derived from at least one impedance value measured for at least one body segment of the reference individual.

Each reference signature can include a reference range based on a distribution of reference impedance indicators associated with reference individuals having a respective body state and respective physical characteristics, so that measured values can be compared to the range to determine a degree of similarity between the subject impedance indicator and the reference signature.

Thus, the processing devices typically analyse the at least one subject impedance indicator by selecting one or more of the reference signatures using the subject characteristic data, generating at least one subject signature indicative of the at least one subject impedance indicator and then comparing the at least one subject signature to the selected reference signatures.

The reference and subject signatures by can also include other body parameter values obtained by performing at least one measurement on one or more other body parameters of the reference individual or subject. The other body parameters can include any one or more of a body parameter value; a weight; a cardiac parameter value; a respiratory parameter value; a blood potassium level; a temperature; a blood pressure; a respiratory rate; a heart rate; and, a blood oxygenation level.

Whilst data can be measured, in one example the processing devices can retrieve medical record data from one or more electronic medical records, the medical record data including any one or more of subject characteristic data, subject body parameter values, reference characteristic data, reference body parameter values or reference body state indications. If this is performed, the processing devices typically retrieve the medical record data using a user identifier of the reference individual or subject, or a medical record identifier related to a user identifier. Thus, in one example, the processing devices determine a user identifier from the user data, retrieve a medical record identifier from an index using the user identifier, generate a query using the medical record identifier, transfer the query to an electronic medical record system and receive medical record data in response to the query.

Alternatively, the processing devices can receive from the measuring device one or more of the subject characteristic data, subject body parameter values, reference characteristic data, reference body parameter values and reference body state indications. Thus, these can be measured by the same apparatus used to perform the impedance measurement or can be measured via alternative mechanisms, such as part of a separate health check and retrieved from stored data such as a medical record.

Having generated the body state indicator, this can be stored, stored as part of an electronic medical record, provided to the client device of a respective measuring system for display to the user or another individual or provided to a client device of a nominated party for display. For example, the body state indicator could be provided to a medical practitioner, allowing them to review this and take appropriate action such as diagnosing a condition and/or administering treatment.

In one example, the measuring device includes a first housing including spaced pairs of foot drive and sense electrodes provided in electrical contact with feet of the subject in use and a second housing including spaced pairs of hand drive and sense electrodes provided in electrical contact with hands of the subject in use. In one example, the client device is at least one of a smart phone and a tablet.

It will be appreciated that features from different examples above may be used interchangeably where appropriate. Furthermore, whilst the above examples have focused on a subject such as a human, it will be appreciated that the measuring device and techniques described above can be used with any animal, including but not limited to, primates, livestock, performance animals, such race horses, or the like. The above described processes can be used for diagnosing the presence, absence or degree of a range of body states, including, but not limited to abnormal hydration, cancer, heart failure, congestive heart failure, oedema, lymphodema, or the like, and reference to specific indicators is not intended to be limiting.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The invention claimed is:

1. A system for determining a body state indicator for a biological subject, the system including:
   a) a number of measuring systems, each measuring system being capable of performing impedance measurements on a user and having:
      i) a measuring device including:
         (1) at least one signal generator electrically connected to drive electrodes to apply a drive signal to a user;
         (2) at least one sensor electrically connected to sense electrodes to measure a response signal in the user;
         (3) a measuring device processor that at least in part:
            (a) controls the at least one signal generator;
            (b) receives an indication of a measured response signal from the at least one sensor; and,
            (c) generates measurement data indicative of at least one measured impedance value; and,
      ii) a client device in communication with the measuring device, wherein the client device:
         (1) receives the measurement data;
         (2) generates user data indicative of the measurement data and a user identifier associated with the user; and,
         (3) communicates the user data via a communication network; and,
   b) one or more one processing devices that:
      i) generate reference signatures by:
         (1) obtaining user data for a plurality of reference individuals from one or more of the number of measuring systems, via the communications network;
         (2) determining for each reference individual, at least in part using respective user data, reference data including:
            (a) at least one reference impedance indicator obtained from user data by performing at least one impedance measurement on the reference individual;
            (b) a reference body state indication indicative of any body states associated with the reference individual; and,
            (c) reference characteristic data indicative of one or more physical characteristics of the reference individual; and,
         (3) analysing the reference data by mining aggregated data for the plurality of reference individuals to establish a plurality of reference signatures, each reference signature being associated with a respective body state for respective physical characteristics and including a plurality of reference ranges, the plurality of reference ranges being based on distributions of different respective reference impedance indicators associated with reference individuals having the respective body state and the respective physical characteristics and the different reference impedance indicators include at least one of:
            (a) impedance values measured for different body segments of the reference individual;
            (b) impedance parameter values derived from impedance values measured for different body segments of the reference individual;
            (c) different impedance parameter values derived from impedance values measured for at least one body segment of the reference individual;
            (d) fluid level indicators indicative of fluid levels in different body segments of the reference individual; or
            (e) fluid level indicators indicative of different fluid levels in at least one body segment of the reference individual; and,
      ii) analyse impedance measurements for a subject by:
         (1) obtaining user data for the subject from one of the number of measuring systems, via the communications network;
         (2) determining, at least in part using the user data for the subject:
            (a) subject characteristic data indicative of one or more physical characteristics of the subject; and,
            (b) at least one subject impedance indicator derived from at least one measured impedance value for the subject; and,
         (3) analysing the at least one subject impedance indicator at least in part using the reference signatures and the subject characteristic data; and,
      iii) generating at least one body state indicator in accordance with the analysis.

2. A system according to claim 1, wherein the subject impedance indicators include at least one of:
   a) at least one impedance value measured for at least one body segment of the subject;
   b) at least one impedance parameter value derived from at least one impedance value measured for at least one body segment of the subject; or,
   c) a fluid level indicator indicative of fluid levels in at least one body segment of the reference individual, the fluid level indicator being derived from at least one impedance value measured for at least one body segment of the subject.

3. A system according to claim 1, wherein the one or more processing devices analyse the at least one subject impedance indicator by:
   a) selecting one or more of the reference signatures using the subject characteristic data;
   b) generating at least one subject signature indicative of the at least one subject impedance indicator; and,
   c) comparing the at least one subject signature to the selected reference signatures.

4. A system according to claim 1, wherein the one or more processing devices:
   a) generate reference signatures by:
      i) determining at least one other reference body parameter value obtained by performing at least one measurement on one or more other body parameters of the reference individual; and,
      ii) generating each reference signature so that each reference signature is indicative of at least one reference impedance indicator and at least one other reference body parameter value associated with a respective body state for respective physical characteristics; and,
b) generate a subject signature by:
  i) determining at least one other subject body parameter value obtained by performing at least one measurement on one or more other body parameters of the subject; and,
  ii) generating the at least one subject signature using the at least one other subject body parameter value.

5. A system according to claim 4, wherein the at least one other reference body parameter value is indicative of at least one of:
a) a body parameter value;
b) a weight;
c) a cardiac parameter value;
d) a respiratory parameter value;
e) a blood potassium level;
f) a temperature;
g) a blood pressure;
h) a respiratory rate;
i) a heart rate; or,
j) a blood oxygenation level.

6. A system according to claim 1, wherein the one or more processing devices retrieve medical record data from one or more electronic medical records, the medical record data including at least one of:
a) subject characteristic data;
b) at least one other subject body parameter value;
c) reference characteristic data;
d) at least one other reference body parameter value; or,
e) a reference body state indication.

7. A system according to claim 6, wherein the one or more processing devices retrieve medical record data using at least one of:
a) a user identifier of a subject;
b) a user identifier of a reference individual; or,
c) a medical record identifier related to a user identifier.

8. A system according to claim 6, wherein the one or more processing devices:
a) determine a user identifier from the user data;
b) retrieve a medical record identifier from an index using the user identifier;
c) generate a query using the medical record identifier;
d) transfer the query to an electronic medical record system; and,
e) receive medical record data in response to the query.

9. A system according to claim 1, wherein the one or more processing devices receive from the measuring device at least one of:
a) subject characteristic data;
b) at least one other subject body parameter value;
c) reference characteristic data;
d) at least one other reference body parameter value; or,
e) a reference body state indication.

10. A system according to claim 1, wherein the one or more processing devices, at least one of:
a) store the at least one body state indicator;
b) store the at least one body state indicator as part of an electronic medical record;
c) provide an indication of the at least one body state indicator to the client device of a respective measuring system for display; or,
d) provide an indication of the at least one body state indicator to a client device of a nominated party for display.

11. A system according to claim 1, wherein the measuring device includes at least one of:
a) a first housing including spaced pairs of foot drive and sense electrodes provided in electrical contact with feet of the subject in use; or,
b) a second housing including spaced pairs of hand drive and sense electrodes provided in electrical contact with hands of the subject in use.

12. A system according to claim 1, wherein the client device is at least one of:
a) a smart phone; or,
b) a tablet.

13. A method for determining a body state indicator for a biological subject, the method including:
a) providing a number of measuring systems, each measuring system being capable of performing impedance measurements on a user and having:
  i) a measuring device including:
    (1) at least one signal generator electrically connected to drive electrodes to apply a drive signal to a user;
    (2) at least one sensor electrically connected to sense electrodes to measure a response signal in the user;
    (3) a measuring device processor that at least in part:
      (a) controls the at least one signal generator;
      (b) receives an indication of a measured response signal from the at least one sensor; and,
      (c) generates measurement data indicative of at least one measured impedance value; and,
    (4) a client device in communication with the measuring device, wherein the client device:
      (a) receives the measurement data;
      (b) generates user data indicative of the measurement data and a user identifier associated with the user; and,
      (c) communicates the user data via a communication network;
b) using one or more one processing devices to:
  i) generate reference signatures by:
    (1) obtaining user data for a plurality of reference individuals from one or more of the number of measuring systems, via the communications network;
    (2) determining for each reference individual, at least in part using respective user data, reference data including:
      (a) at least one reference impedance indicator obtained from user data by performing at least one impedance measurement on the reference individual;
      (b) a reference body state indication indicative of any body states associated with the reference individual; and,
      (c) reference characteristic data indicative of one or more physical characteristics of the reference individual; and,
    (3) analysing the reference data by mining aggregated data for the plurality of reference individuals to establish a plurality of reference signatures, each reference signature associated with a respective body state for respective physical characteristics and including a plurality of reference ranges, the plurality of reference ranges being based on distributions of different respective reference impedance indicators associated with reference individuals having the respective body state and the respective physical characteristics and the reference impedance indicators including at least one of:
   (a) impedance values measured for different body segments of the reference individual;
   (b) impedance parameter values derived from impedance values measured for different body segments of the reference individual;
   (c) different impedance parameter values derived from impedance values measured for at least one body segment of the reference individual;
   (d) fluid level indicators indicative of fluid levels in different body segments of the reference individual; or,
   (e) fluid level indicators indicative of different fluid levels in at least one body segment of the reference individual;
ii) analyse impedance measurements for a subject by:
   (1) obtaining user data for the subject from one of the number of measuring systems, via the communications network;
   (2) determining, at least in part using the user data for the subject:
     (a) subject characteristic data indicative of one or more physical characteristics of the subject; and,
     (b) at least one subject impedance indicator derived from at least one measured impedance value for the subject; and,
   (3) analysing the at least one subject impedance indicator at least in part using the reference signatures and the subject characteristic data; and,
iii) generate at least one body state indicator in accordance with the analysis.

14. A system for determining reference signatures for use in assisting identification of a body state in a biological subject, the system including at least one processing device that:
   a) obtains reference data for each of a plurality of reference individuals, the reference data including:
     i) at least one reference impedance indicator obtained by performing at least one impedance measurement on the reference individual;
     ii) a body state indication indicative of any body states associated with the reference individual; and,
     iii) characteristic data indicative of one or more physical characteristics of the reference individual; and,
   b) analyses the reference data by mining aggregated data for the plurality of reference individuals to establish a plurality of reference signatures, each reference signature being associated with a respective body state for respective physical characteristics and including a plurality of reference ranges, the plurality of reference ranges being based on distributions of different respective reference impedance indicators associated with reference individuals having the respective body state and the respective physical characteristics and the reference impedance indicators including at least one of:
     i) impedance values measured for different body segments of the reference individual;
     ii) impedance parameter values derived from impedance values measured for different body segments of the reference individual;
     iii) different impedance parameter values derived from impedance values measured for at least one body segment of the reference individual;
     iv) fluid level indicators indicative of fluid levels in different body segments of the reference individual; or,
     v) fluid level indicators indicative of different fluid levels in at least one body segment of the reference individual.

15. A system according to claim 14, wherein the reference impedance indicators are obtained for at least some of the reference individuals, at least one of:
   a) for each of a plurality of body segments;
   b) at a number of different times; or,
   c) repeatedly over a time period.

16. A system according to claim 14, wherein at least one reference impedance indicator is one of a number of reference body parameter values, the reference data further including at least one other reference body parameter value obtained by performing at least one measurement on one or more other body parameters of the reference individual, and wherein each reference signature is indicative of at least one reference impedance indicator and at least one other reference body parameter value associated with a respective body state for respective physical characteristics.

17. A system according to claim 16, wherein the at least one other reference body parameter value is indicative of at least one of:
   a) a body parameter value;
   b) a weight;
   c) a cardiac parameter value;
   d) a respiratory parameter value;
   e) a blood potassium level;
   f) a temperature;
   g) a blood pressure;
   h) a respiratory rate;
   i) a heart rate; or,
   j) a blood oxygenation level.

18. A system for use in assisting identification of a body state in a biological subject, wherein the system includes in at least one processing device:
   a) determining subject data for the biological subject, the subject data including:
     i) at least one subject impedance indicator obtained by performing at least one impedance measurement on the subject; and,
     ii) subject characteristic data indicative of one or more physical characteristics of the subject; and,
   b) using the subject data and reference signatures to generate a body state indicator, each reference signature being associated with a respective body state for respective physical characteristics, and being derived by mining aggregated data of the plurality of reference individuals, wherein each reference signature includes a plurality of reference ranges, the plurality of reference ranges being based on distributions of different respective reference impedance indicators associated with reference individuals having the respective body state and the respective physical characteristics and the reference impedance indicators including at least one of:
     i) impedance values measured for different body segments of the reference individual;
     ii) impedance parameter values derived from impedance values measured for different body segments of the reference individual;
     iii) different impedance parameter values derived from impedance values measured for at least one body segment of the reference individual;

iv) fluid level indicators indicative of fluid levels in different body segments of the reference individual; or,
v) fluid level indicators indicative of different fluid levels in at least one body segment of the reference individual.

\* \* \* \* \*